(12) United States Patent
Coates et al.

(10) Patent No.: US 11,066,386 B2
(45) Date of Patent: Jul. 20, 2021

(54) CGRP RECEPTOR ANTAGONISTS

(71) Applicant: Eli Lilly and Company, Indianapolis, IN (US)

(72) Inventors: David Andrew Coates, New Palestine, IN (US); Simon James Richards, Bordon (GB); Adam Jan Sanderson, Camberley (GB)

(73) Assignee: Eli Lilly and Company, Indianapolis, IN (US)

(*) Notice: Subject to any disclaimer, the term of this patent is extended or adjusted under 35 U.S.C. 154(b) by 51 days.

(21) Appl. No.: 16/607,902

(22) PCT Filed: May 8, 2018

(86) PCT No.: PCT/US2018/031483
§ 371 (c)(1),
(2) Date: Oct. 24, 2019

(87) PCT Pub. No.: WO2018/213056
PCT Pub. Date: Nov. 22, 2018

(65) Prior Publication Data
US 2020/0181111 A1   Jun. 11, 2020

Related U.S. Application Data

(60) Provisional application No. 62/506,195, filed on May 15, 2017.

(51) Int. Cl.
*C07D 401/12*   (2006.01)
*A61P 25/06*    (2006.01)

(52) U.S. Cl.
CPC ............ *C07D 401/12* (2013.01); *A61P 25/06* (2018.01); *C07B 2200/13* (2013.01)

(58) Field of Classification Search
CPC .... C07D 401/12; A61P 25/06; C07B 2200/13
See application file for complete search history.

(56) References Cited

U.S. PATENT DOCUMENTS

| | | |
|---|---|---|
| 6,680,387 B2 | 1/2004 | Drzgala et al. |
| 10,336,726 B2 | 7/2019 | McMahon et al. |
| 2015/0203496 A1 | 7/2015 | Bell et al. |
| 2017/0044138 A1 | 2/2017 | Coates et al. |
| 2017/0044163 A1 | 2/2017 | Coates et al. |

*Primary Examiner* — John Mabry
(74) *Attorney, Agent, or Firm* — Nelsen L Lentz

(57) ABSTRACT

The present invention provides compounds of Formula II or a pharmaceutically acceptable salts thereof, useful as a CGRP receptor antagonist.

Formula II

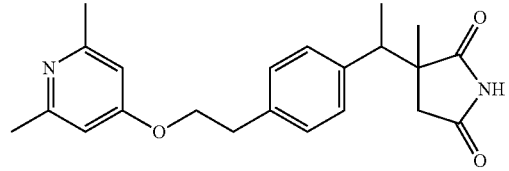

11 Claims, No Drawings

CGRP RECEPTOR ANTAGONISTS

The present invention relates to certain novel calcitonin gene-related peptide (CGRP) receptor antagonist compounds, to pharmaceutical compositions comprising the compounds, to methods of using the compounds to prevent or treat certain physiological disorders such as migraine, and to intermediates and processes useful in the synthesis of the compounds.

The present invention is in the field of prevention and treatment of migraine and other neurological diseases and disorders thought to be mediated by CGRP (See for example, S. Benemei, et. al., *Current Opinion in Pharmacology*, 9, 9-14 (2009)). Migraine is a debilitating disease suffered by millions of people worldwide. Treatment options for migraine include the triptans, such as sumatriptan and zolmitriptan. Unfortunately, currently approved agents available to the patient do not always provide effective treatment, and these agents can be associated with various untoward side effects such as dizziness, paresthesia, and chest discomfort. In addition, triptans possess certain cardiovascular concerns causing them to be contraindicated in patients suffering from substantial underlying cardiovascular disease or uncontrolled hypertension (See T. W. Ho, et. al., *The Lancet*, 372, 2115-2123 (2008)). Thus, there is a significant unmet need in the prevention and treatment of migraine. CGRP receptor antagonists are desired to provide more effective treatment for or prevention of certain neurological diseases, such as migraine.

United States Publication Nos. 2017/0044138 A1 and 2017/0044163 each disclose certain CGRP receptor antagonist compounds useful in the treatment or prevention of migraine. U.S. Pat. No. 6,680,387 discloses certain 5-benzyl- or 5-benzylidene-thiazolidine-2,4-diones for the treatment of type-II diabetes mellitus, atherosclerosis, hypercholesterolemia, and hyperlipidemia.

The present invention provides certain novel compounds that are antagonists of the CGRP receptor. The present invention also provides antagonists of the CGRP receptor that are centrally penetrant.

Accordingly, the present invention provides a compound of Formula I:

Formula I

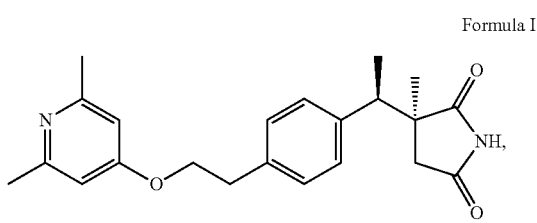 [SMILES: Cc1cc(OCCc2ccc([C@@H](C)[C@]3(C)CC(=O)NC3=O)cc2)cc(C)n1]

or a pharmaceutically acceptable salt thereof.

The present invention further provides a compound of Formula II:

Formula II

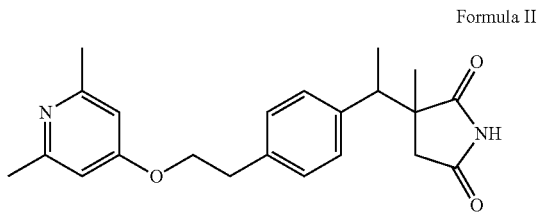 [SMILES: Cc1cc(OCCc2ccc(C(C)C3(C)CC(=O)NC3=O)cc2)cc(C)n1]

or a pharmaceutically acceptable salt thereof.

The present invention also provides a method of preventing migraine in a patient, comprising administering to a patient in need thereof an effective amount of a compound of Formula I or Formula II, or a pharmaceutically acceptable salt thereof.

The present invention further provides a method of treating migraine in a patient, comprising administering to a patient in need thereof an effective amount of a compound of Formula I or Formula II, or a pharmaceutically acceptable salt thereof. The present invention also provides a method of antagonizing the CGRP receptor in a patient, comprising administering to a patient in need thereof an effective amount of a compound of Formula I or Formula II, or a pharmaceutically acceptable salt thereof.

Furthermore, this invention provides a compound of Formula I or Formula II, or a pharmaceutically acceptable salt thereof for use in therapy, in particular for the treatment of migraine. In addition, this invention provides a compound of Formula I or Formula II, or a pharmaceutically acceptable salt thereof for use in preventing migraine. Even furthermore, this invention provides the use of a compound of Formula I or Formula II, or a pharmaceutically acceptable salt thereof, for the manufacture of a medicament for the treatment of migraine or for preventing migraine.

The invention further provides a pharmaceutical composition, comprising a compound of Formula I or Formula II, or a pharmaceutically acceptable salt thereof, with one or more pharmaceutically acceptable carriers, diluents, or excipients. The invention further provides a process for preparing a pharmaceutical composition, comprising admixing a compound of Formula I or Formula II, or a pharmaceutically acceptable salt thereof, with one or more pharmaceutically acceptable carriers, diluents, or excipients. This invention also encompasses novel intermediates and processes for the synthesis of the compounds of Formula I and Formula II. For example, the invention further provides the following intermediate:

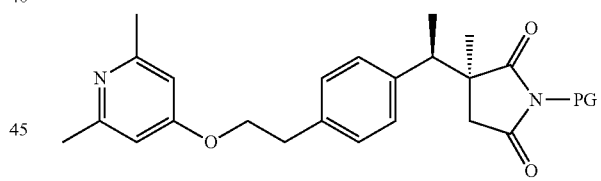

wherein PG is a suitable protecting group. Examples of suitable protecting groups are triphenylmethyl, p-methoxybenzyl, and the like.

As used herein, the terms "treating", "treatment", or "to treat" includes restraining, slowing, stopping, or reversing the progression or severity of an existing symptom or disorder.

As used herein, the term "preventing" or "prevention" refers to protecting a patient who is prone to a certain disease or disorder, such as migraine, but is not currently suffering from symptoms of the disease or disorder, such as symptoms of migraine.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

Compounds of the present invention are effective at a dosage per day that falls within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I and Formula II, or pharmaceutically acceptable salts thereof are particularly useful in the prevention and treatment methods of the invention, but certain groups, substituents, and configurations are preferred. The following paragraphs describe such preferred groups, substituents, and configurations. Although the present invention contemplates all individual enantiomers and diastereomers, as well as mixtures of the enantiomers of said compounds, including racemates, the compounds with absolute configuration as set forth below are especially preferred. It is understood that these preferences are applicable both to the prevention and treatment methods and to the new compounds of the invention.

The following compounds are preferred:

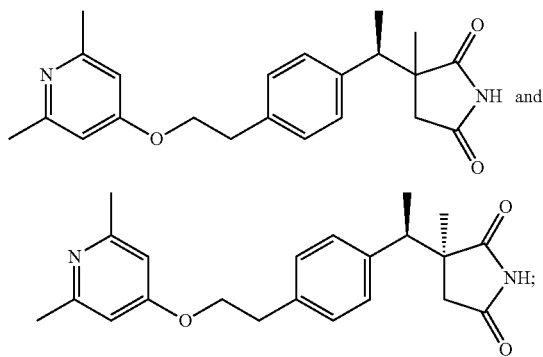

and the pharmaceutically acceptable salts thereof.

The following compound is more preferred:

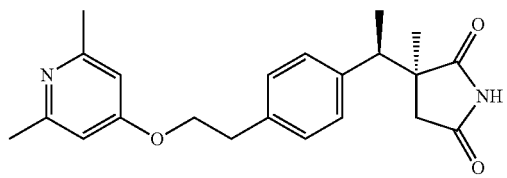 [SMILES: Cc1cc(OCCc2ccc([C@@H](C)[C@]3(C)CC(=O)NC3=O)cc2)cc(C)n1]

and the pharmaceutically acceptable salts thereof.

(3S)-3-[(1R)-1-[4-[2-[(2,6-dimethyl-4-pyridyl)oxy]ethyl]phenyl]ethyl]-3-methyl-pyrrolidine-2,5-dione mesylate is also preferred. Crystalline (3S)-3-[(1R)-1-[4-[2-[(2,6-dimethyl-4-pyridyl)oxy]ethyl]phenyl]ethyl]-3-methyl-pyrrolidine-2,5-dione mesylate is further preferred.

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See, for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

A pharmaceutically acceptable salt of the compounds of the invention, such as a hydrochloride salt, can be formed, for example, by reaction of an appropriate free base of a compound of the invention, an appropriate pharmaceutically acceptable acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," International Journal of Pharmaceutics, 33: 201-217 (1986); Bastin, R. J., et al. "Salt Selection and Optimization Procedures for Pharmaceutical New Chemical Entities," Organic Process Research and Development, 4: 427-435 (2000); and Berge, S. M., et al., "Pharmaceutical Salts," Journal of Pharmaceutical Sciences, 66: 1-19, (1977).

Certain abbreviations are defined as follows: "ACN" refers to acetonitrile; "c-Pr" refers to cyclopropyl; "DCM" refers to DCM or methylene chloride; "DMEA" refers to N,N-dimethyl ethyl amine; "DIPEA" refers to N,N-diisopropylethylamine; "DMF" refers to N,N-dimethylformamide; "DMSO" refers to dimethylsulfoxide; "Et" refers to ethyl; "Et$_2$O" refers to diethyl ether; "EtOAc" refers to ethyl acetate; "EtOH" refers to ethanol; "g" when used in reference to centrifugation, refers to relative centrifugal force; "HPLC" refers to high Performance Liquid Chromatography; "HOBt" refers to hydroxybenzotriazole; "hr" refers to hour or hr; "HATU" refers to 1-[Bis(dimethylamino)methylene]-1H-1,2,3-triazolo[4,5-b]pyridinium 3-oxid hexafluorophosphate or N-[(dimethylamino)-1H-1,2,3-triazolo-[4,5-b]pyridin-1-ylmethylene]-N-methylmethanaminium hexafluorophosphate N-oxide; "HTRF" refers to Homogeneous Time Resolved Fluorescence; "IC$_{50}$" refers to the concentration of an agent that produces 50% of the maximal inhibitory response possible for that agent; "kPa" refers to kilopascal or kilopascals; "kV" refers to kilovolts; "LAH" refers to lithium aluminum hydride; "LC-ES/MS" refers to Liquid Chromatography Electrospray Mass Spectrometry; "LDA" refers to lithium diisopropylamide; "mA" refers to milliamps or milliamperes; "MDCK" refers to Madin-Darby canine kidney epithelial cells; "min" refers to minute or minutes; "Me" refers to methyl; "MeOH" refers to methanol or methyl alcohol; "MTBE" refers to methyl-tent-butyl ether; "NaHMDS" refers to sodium bis(trimethylsilyl)amide; "n-BuLi" refers to n-butyllithium; "PMB" refers to p-methoxybenzyl or 4-methoxybenzyl; "psi" refers to pounds per square inch; "rpm" refers to revolutions per minute; "RT" refers to room temperature; "SEM" refers to standard error of the mean; "SFC" refers to Supercritical Fluid Chromatography; "T3P" refers to 2,4,6-tripropyl-1,3, 5,2,4,6-trioxatriphosphorinane-2,4,6-trioxide solution; "t-BuOH" refers to tert-butanol; "TEA" refers to triethylamine; "TFA" refers to trifluoroacetic acid; "THF" refers to tetrahydrofuran; "TMEDA" refers to tetrametylethylenediamine; "t$_R$" refers to retention time; "Tr" refers to trityl or triphenylmethyl; "U/mL" refers to units per milliliter.

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, examples, and assays further illustrate the invention, but should not be construed to limit the scope of the invention in any way.

Scheme 1

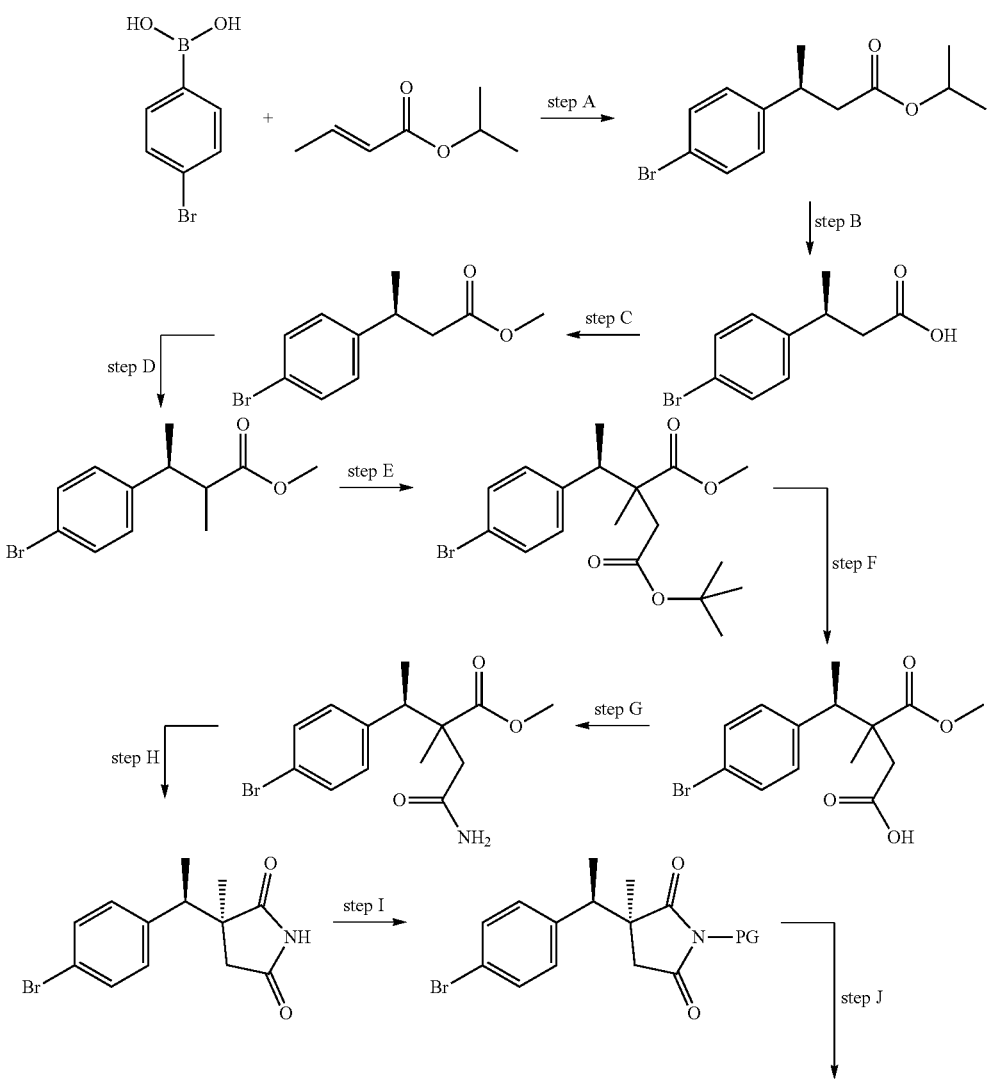

-continued

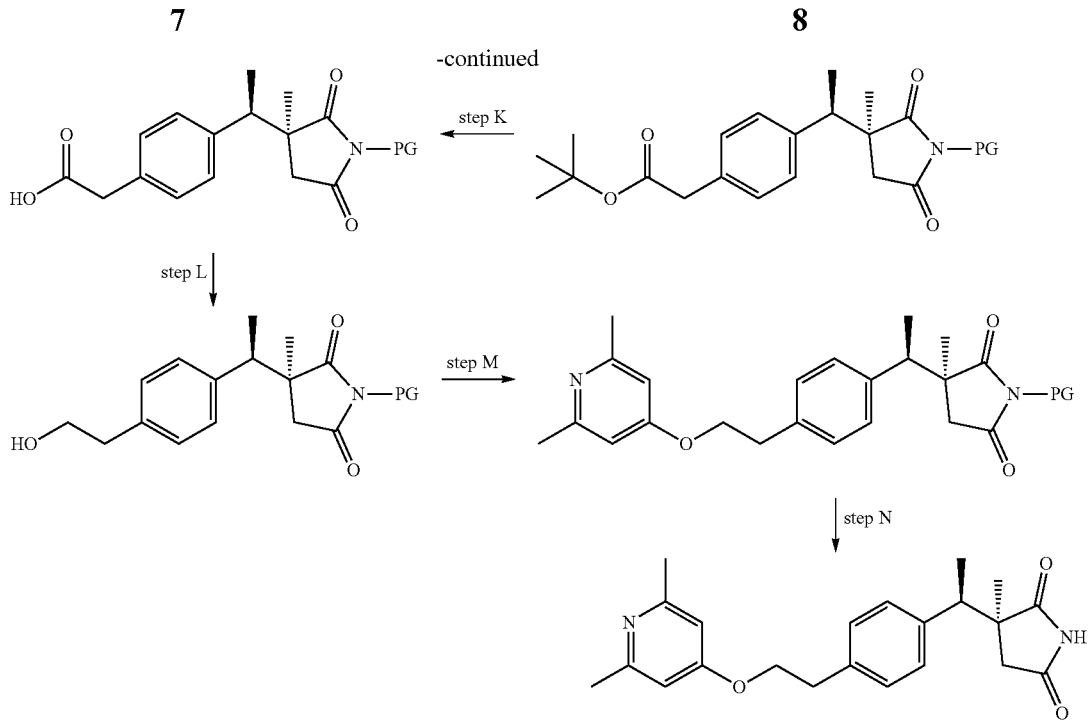

Scheme 1 depicts the synthesis of (3S)-3-[(1R)-1-[4-[2-[(2,6-dimethyl-4-pyridyl)oxy]ethyl]phenyl]ethyl]-3-methyl-pyrrolidine-2,5-dione. In Scheme 1, step A, asymmetric arylation of isopropyl (E)-but-2-enoate may be accomplished under coupling conditions using transition-metal catalysts, such as rhodium, as is well-described in the art. Generally, an aryl boronic acid may be coupled to isopropyl (E)-but-2-enoate to yield rhodium catalysis product isopropyl (3S)-3-(4-bromophenyl)butanoate with high enantioselectivity. For example, about 1.05-1.1 equivalents of 4-bromophenyl boronic acid may be treated with about 0.01 equivalents of a rhodium catalyst, specifically, bis(norbornadiene)rhodium(I) tetrafluoroborate, followed by addition of an appropriate chiral ligand such as 0.01-0.015 equivalents (R)-(+)-2,2'-bis(diphenylphosphino)-1,1'-binaphthyl, about 1 equivalent TEA, and about 1 equivalent of isopropyl (E)-but-2-enoate in an appropriate solvent mixture such as wet 1,4-dioxane or THF and water (about 8:1). The resulting reaction mixture may be heated to about 40° C. for about 18 hr. The product can then be isolated and purified utilizing techniques well known in the art, such as extraction methods and chromatography. For example, the reaction mixture may be diluted with water and extracted with an appropriate nonpolar organic solvent such as MTBE or DCM. The organic extracts may be combined, dried over anhydrous Na$_2$SO$_4$, filtered, and concentrated under reduced pressure to provide the crude product of step A. The crude product may then be purified by flash chromatography on silica gel with a suitable eluent, such as hexanes/EtOAc gradient, to provide the purified product of step A, isopropyl (3S)-3-(4-bromophenyl)butanoate in high enantiomeric excess.

In Scheme 1, step B, hydrolysis of the product from Scheme 1, step A, may be accomplished under saponification conditions well known in the art. For example, isopropyl (3S)-3-(4-bromophenyl)butanoate may be dissolved in an appropriate alcoholic solvent such as MeOH and treated with an excess of aqueous mineral base such as NaOH. After heating for about 1 hr, the product can then be isolated and purified utilizing techniques well known in the art, such as extraction, trituration, and evaporation methods. For example, the reaction mixture may be extracted with an appropriate organic solvent such as DCM and the resulting separated aqueous layer may be treated with an excess of a mineral acid such as conc. HCl to pH~4. The acidified aqueous layers may then be extracted with an appropriate organic solvent such as DCM. The organic extracts may be combined, dried over anhydrous Na$_2$SO$_4$, filtered, and concentrated under reduced pressure to provide the crude product of step B. The crude product may be triturated with a non-polar organic solvent such as heptanes, the resulting precipitates may be filtered away, and the filtrate may be concentrated under reduced pressure to obtain the product of step B, (3S)-3-(4-bromophenyl)butanoic acid, in very high enantiomeric excess.

In Scheme 1, step C, esterification of the product from Scheme 1, step B, may be carried out under a wide range of acidic/basic esterification methods well known in the art, or by direct esterification with diazomethane. For example, (3S)-3-(4-bromophenyl)butanoic acid dissolved in an appropriate alcoholic solvent such as MeOH may be treated with an excess of a mineral acid, such as conc. H$_2$SO$_4$. The resulting mixture may be heated for about 2 hr, and the product can then be isolated by utilizing techniques well known in the art, such as extraction. The reaction mixture may be concentrated under reduced pressure, and the resulting residue may be partitioned between water and a suitable organic solvent such as MTBE. The organic extracts may be combined, washed with water, dried over anhydrous MgSO$_4$, filtered, and concentrated under reduced pressure to provide the product of step C, methyl (3S)-3-(4-bromophenyl)-butanoate, suitable for use without additional purification.

In Scheme 1, step D, alkylation of the product of scheme 1, step C, may be achieved using variety of alkylation conditions well known in the literature. For example, methylation of methyl (3S)-3-(4-bromophenyl)butanoate may be accomplished by treatment with about 1.5-1.75 equivalents of a non-nucleophilic base such as n-BuLi in an appropriate solvent such as anhydrous THF at low temperature followed by quenching of the resulting anion with about 1.5-1.6 equivalents $CH_3I$. The product can then be isolated by utilizing techniques well known in the art, such as extraction. The reaction mixture may be partitioned between water and an appropriate organic solvent such as MTBE. The combined organic extracts may be washed sequentially with water, saturated aqueous NaCl, dried over $MgSO_4$, filtered, and concentrated under reduced pressure to obtain the product of step D, (3S,2R/S)-methyl 3-(4-bromophenyl)-2-methylbutanoate, as a mixture of diastereomers suitable for use without additional purification.

In Scheme 1, step E, the product of Scheme 1, step D, (3S,2R/S)-methyl 3-(4-bromophenyl)-2-methylbutanoate as a mixture of diastereomers, may be treated with about 1 equivalent of an organic base such as n-butyllithium in an appropriate organic solvent such as anhydrous THF at low temperature. The resulting mixture may then be treated with a solution of about 0.9 equivalents tert-butyl 2-bromoacetate. The product can then be isolated by utilizing techniques well known in the art, such as extraction. The reaction mixture may be partitioned between water and an appropriate organic solvent such as MTBE, and the combined organic extracts may be washed sequentially with water and saturated aqueous NaCl. The organic extracts may be dried over $MgSO_4$, filtered, and concentrated under reduced pressure to obtain the product of step E, 4-(tert-butyl) 1-methyl (S/R)-2-((R)-1-(4-bromophenypethyl)-2-methylsuccinate, as a mixture of diastereomers suitable for use without additional purification.

In Scheme 1, step F, a mixture of the diastereomeric esters from the product of Scheme 1, step E, may be hydrolyzed under conditions well known in the prior art. For example, 4-(tert-butyl) 1-methyl (S/R)-2-((R)-1-(4-bromophenyl) ethyl)-2-methylsuccinate may be dissolved in an appropriate organic solvent such as DCM and treated with an excess or an organic acid such as TFA. The resulting mixture may be stirred at RT for about 18 hr, and the product can then be isolated by utilizing techniques well known in the art, such as extraction. The reaction mixture may be washed sequentially with water and saturated aqueous NaCl, the organic extracts may be dried over $MgSO_4$, filtered and concentrated under reduced pressure to obtain the product of step F, (3S/R,4R)-4-(4-bromophenyl)-3-(methoxycarbonyl)-3-methylpentanoic acid, as a mixture of diastereomers suitable for use without additional purification.

In Scheme 1, step G, a mixture of the diastereomers from Scheme 1, step F, (3S/R,4R)-4-(4-bromophenyl)-3-(methoxycarbonyl)-3-methylpentanoic acid, may be dissolved in an appropriate polar organic solvent such as anhydrous DMF and treated sequentially with a non-nucleophilic base such as about 3 equivalents of TEA or DIPEA, about 1.2 equivalents of an amide coupling reagent such as HATU, and a solution of excess methanolic ammonia. The resulting mixture may be stirred at RT for about 2-12 hr, and the product can then be isolated by utilizing techniques well known in the art, such as extraction. The reaction mixture may be partitioned between water and an appropriate organic solvent such as DCM, the layers may be separated, and the combined organic extracts are washed sequentially with water and saturated aqueous NaCl. The extracts may then be dried over $MgSO_4$, filtered, and concentrated under reduced pressure to obtain the product of step G, methyl (2S/R)-4-amino-2-[(1R)-1-(4-bromophenyl)ethyl]-2-methyl-4-oxo-butanoate, as a mixture of diastereomers suitable for use without additional purification.

In Scheme 1, step H, a mixture of the diastereomeric product of Scheme 1, step G may be cyclized by heating in the presence of a non-nucleophilic base followed by separation of diastereomers under chiral chromatography conditions. For example, methyl (2S/R)-4-amino-2-[(1R)-1-(4-bromophenyl)ethyl]-2-methyl-4-oxo-butanoate may be dissolved in a mixture of THF/water (about 1:1), treated with about 2.5 equivalents of a non-nucleophilic base such as sodium carbonate, and the resulting mixture may be heated to about 60° C. for about 2 hr. The product can then be isolated by utilizing techniques well known in the art, such as extraction followed by separation of the diastereomers under chiral chromatography conditions. For example, the reaction mixture is extracted with EtOAc, the combined organic extracts are dried over $MgSO_4$, filtered, and concentrated under reduced pressure to give a crude mixture of diastereomers. The diastereomers may be separated by chiral SFC technology, using an isocratic solvent system of EtOH containing a small amount of a non-nucleophilic amine such as N,N-diethylmethylamine/$CO_2$ (about 1:9) to obtain the separated products of step H, (3S)-3-[(1R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione.

The succinimide nitrogen of (3S)-3-[(1R)-1-(4-bromophenyl)ethyl]-3-methyl-pyrrolidine-2,5-dione may be protected with a suitable protecting group under conditions well known in the art, as shown in Scheme 1, step I. For example, about 1 equivalent of (3S)-3-[(1R)-1-(4-bromophenyl) ethyl]-3-methyl-pyrrolidine-2,5-dione may be dissolved in a suitable polar organic solvent, such as DMF, treated with a suitable mild inorganic base, such as $Cs_2CO_3$, followed by addition of about 1 equivalent of 1-(chloromethyl)-4-methoxy-benzene. The resulting mixture may be heated at about 40° C. for about 2 hr, and the product may be isolated by utilizing techniques well known in the art, such as extraction and chromatography. For example, the reaction mixture may be poured over a saturated aqueous solution of $NH_4Cl$, extracted three times with an appropriate organic solvent, such as DCM or EtOAc, and the organic layer may be separated, dried over $MgSO_4$, filtered, and concentrated under reduced pressure. The resulting crude product may be purified by flash chromatography on silica, eluting with a suitable organic solvent mixture, such as EtOAc/hexane, to provide (3S)-3-[(1R)-1-(4-bromophenyl)ethyl]-1-[(4-methoxyphenyl)methyl]-3-methyl-pyrrolidine-2,5-dione the product of Scheme 1, step I.

In Scheme 1, step J, a Negishi coupling of an aryl bromide and an alkylzinc may be accomplished in the presence of a transition metal catalyst, such as palladium or nickel, as is well-described in the art. For example, about 1 equivalent of (3S)-3-[(1R)-1-(4-bromophenyl)ethyl]-1-[(4-methoxyphenyl)methyl]-3-methyl-pyrrolidine-2,5-dione and about 0.1 equivalents of an appropriate palladium-ligand complex, such as bis(tri-tert-butylphosphine)palladium(0), in a suitable polar organic solvent, such as 1,4-dioxane, THF, or DMF, may be treated with a solution of 2-tert-butoxy-2-oxoethylzinc chloride in an appropriate solvent, such as $Et_2O$ or THF, under an atmosphere of nitrogen. The reaction mixture may be heated to about 50-60° C. for about 6-12 hr. The product may be isolated by utilizing techniques well known in the art, such as extraction and chromatography. For example, the reaction mixture may be poured over a saturated aqueous solution of $NH_4Cl$, extracted three times with an appropriate organic solvent, such as DCM or $Et_2O$, and the organic layer may be separated, dried over MgSO$_4$, filtered, and concentrated under reduced pressure. The resulting crude product may be purified by flash chromatography on silica, eluting with a suitable organic solvent mixture, such as EtOAc/hexane, to provide tert-butyl 2-[4-[(1R)-1-[(3S)-1-[(4-methoxyphenyl)methyl]-3-methyl-2,5-dioxo-pyrrolidin-3-yl]ethyl]phenyl]acetate, the product of Scheme 1, step J.

In Scheme 1, step K, tert-butyl 2-[4-[(1R)-1-[(3S)-1-[(4-methoxyphenyl)methyl]-3-methyl-2,5-dioxo-pyrrolidin-3-yl]ethyl]phenyl]acetate, the product of Scheme 1, step J, may be hydrolyzed to obtain the corresponding carboxylic acid, under conditions well known in the art. For example, about 1 equivalent of tert-butyl 2-[4-[(1R)-1-[(3S)-1-[(4-methoxyphenyl)methyl]-3-methyl-2,5-dioxo-pyrrolidin-3-yl]ethyl]phenyl]acetate may be dissolved in a suitable organic solvent, such as DCM, and treated with an excess of TFA, After stirring at RT for about 2-4 hr, the product may be isolated by utilizing techniques well known in the art, such as extraction. For example, the reaction mixture may be concentrated under reduced pressure, and the residue partitioned between saturated aqueous NaCl and CHCl$_3$. The organic layer may be separated, dried over MgSO$_4$, filtered, and concentrated under reduced pressure, to obtain 2-[4-[(1R)-1-[(3S)-1-[(4-methoxyphenyl)methyl]-3-methyl-2,5-dioxo-pyrrolidin-3-yl]ethyl]phenyl]acetic acid, the product of Scheme 1, step K, of sufficient purity for use without additional purification.

In Scheme 1, step L, the acid moiety of 2-[4-[(1R)-1-[(3S)-1-[(4-methoxyphenyl)-methyl]-3-methyl-2,5-dioxo-pyrrolidin-3-yl]ethyl]phenyl]acetic acid may be reduced under an array of conditions well known in the art, including reduction with diborane, alumimun hydride, or borohydrides. For example, about 1 equivalent of 2-[4-[(1R)-1-[(3S)-1-[(4-methoxyphenyl)methyl]-3-methyl-2,5-dioxo-pyrrolidin-3-yl]ethyl]phenyl]acetic acid may be suspended in a suitable polar organic solvent, such as THF or 1,4-dioxane, and treated with about 2 equivalents borane dimethyl sulfide complex at about RT to about 60° C. for about 2-4 hr. The reaction mixture may be quenched with MeOH at RT to about 60° C. for about 1-2-hr. The product may be isolated by utilizing techniques well known in the art, such as extraction and chromatography. For example, the reaction mixture may be poured into saturated aqueous NaHCO$_3$, and extracted twice with EtOAc. The organic extracts may be separated, dried over MgSO$_4$, filtered, and concentrated under reduced pressure. The resulting residue may be purified by flash chromatography on silica, eluting with a suitable organic solvent mixture, such as EtOAc/hexane, to provide (3S)-3-[(1R)-1-[4-(2-hydroxyethyl)phenyl]ethyl]-1-[(4-methoxyphenyl)methyl]-3-methyl-pyrrolidine-2,5-dione, the product of Scheme 1, step L.

In Scheme 1, step M, the alkyl alcohol (3S)-3-[(1R)-1-[4-(2-hydroxyethyl)-phenyl]ethyl]-1-[(4-methoxyphenyl)methyl]-3-methyl-pyrrolidine-2,5-dione, product of Scheme 1, step L, may be arylated under transition-metal-mediated Ullman or Buchwald-Hartwig etherification conditions as described in the literature (B. Liu, B.-F. Shi, *Tet. Lett* 56 (1), Jan. 1, 2015, pp. 15-22). For example, about 1 equivalent (3S)-3-[(1R)-1-[4-(2-hydroxyethyl)phenyl]ethyl]-1-[(4-methoxyphenyl)methyl]-3-methyl-pyrrolidine-2,5-dione and about 2 equivalents 4-bromo-2,6-dimethyl-pyridine may be heated to about 85° C. in a nitrogen purged suitable solvent, such as toluene, in the presence of about 0.1-0.2 equivalents of a suitable palladium-ligand-base mixture (1:4:100 mixture), including Pd(OAc)$_2$ or tris(dibenzylideneacetone)dipalladium(0) with 2-(di-tert-butylphosphino)-2',4',6'-triisopropyl-3,6-dimethoxy-1,1'-biphenyl and Cs$_2$CO$_3$, tris(dibenzylideneacetone) dipalladium(0) with 2-(di-tert-butylphosphino)-2',4',6'-triisopropyl-3,6-dimethoxy-1,1'-biphenyl and Cs$_2$CO$_3$, or chloro[2-(dicyclohexylphosphino)-3,6-dimethoxy-2',4',6'-triisopropyl-1,1'-biphenyl][2-(2-aminoethyl)phenyl]palladium(II) with Cs$_2$CO$_3$. The product may be isolated by utilizing techniques well known in the art, such as extraction and chromatography. For example, the reaction mixture may be poured into saturated aqueous NH$_4$Cl, and extracted twice with a suitable organic solvent, e.g., EtOAc or DCM. The organic extracts may be separated, dried over MgSO$_4$, filtered, and concentrated under reduced pressure. The resulting residue may be purified by flash chromatography on silica, eluting with a suitable organic solvent mixture, such as EtOAc/hexane, to provide (3S)-3-[(1R)-1-[4-[2-[(2,6-dimethyl-4-pyridyl)oxy]ethyl]phenyl]ethyl]-1-[(4-methoxyphenyl)methyl]-3-methyl-pyrrolidine-2,5-dione, the product of Scheme 1, step M.

Scheme 1, step N, depicts the removal of the PMB group and may be accomplished under an array of conditions as is well known to a skilled artisan. For example, about 1 equivalent (3S)-3-[(1R)-1-[4-[2-[(2,6-dimethyl-4-pyridyl)oxy]ethyl]-phenyl]ethyl]-1-[(4-methoxyphenyl)methyl]-3-methyl-pyrrolidine-2,5-dione, the product of Scheme 1, step M, may be dissolved in a suitable solvent or mixture, e.g., ACN and water, about 4 equivalents of ceric ammonium nitrate may be added, and the mixture may be stirred for about 2 h. The reaction may be quenched by the addition of a suitable aqueous mineral base, such as aqueous NaOH. The product may be isolated by utilizing techniques well known in the art, such as neutralization, extraction and chromatography. For example, the basic mixture may be acidified to about pH 3 with a suitable aqueous mineral acid such as HCl, and the resulting mixture may be extracted with a suitable organic solvent mixture, e.g., CHCl$_3$/EtOH, filtered through diatomaceous earth. The organic extract may be separated, dried over MgSO$_4$, filtered, and concentrated under reduced pressure. The resulting residue may be purified by reverse phase column chromatography using a suitably buffered polar/organic mixture, e.g., MeOH/ACN buffered with about 10 mM aqueous NH$_4$HCO$_3$, to provide the desired product of Scheme 1, step N, (3 S)-3-[(1R)-1-[4-[2-[(2,6-dimethyl-4-pyridyl)oxy]ethyl]phenyl]ethyl]-3-methyl-pyrrolidine-2,5-dione.

Scheme 2

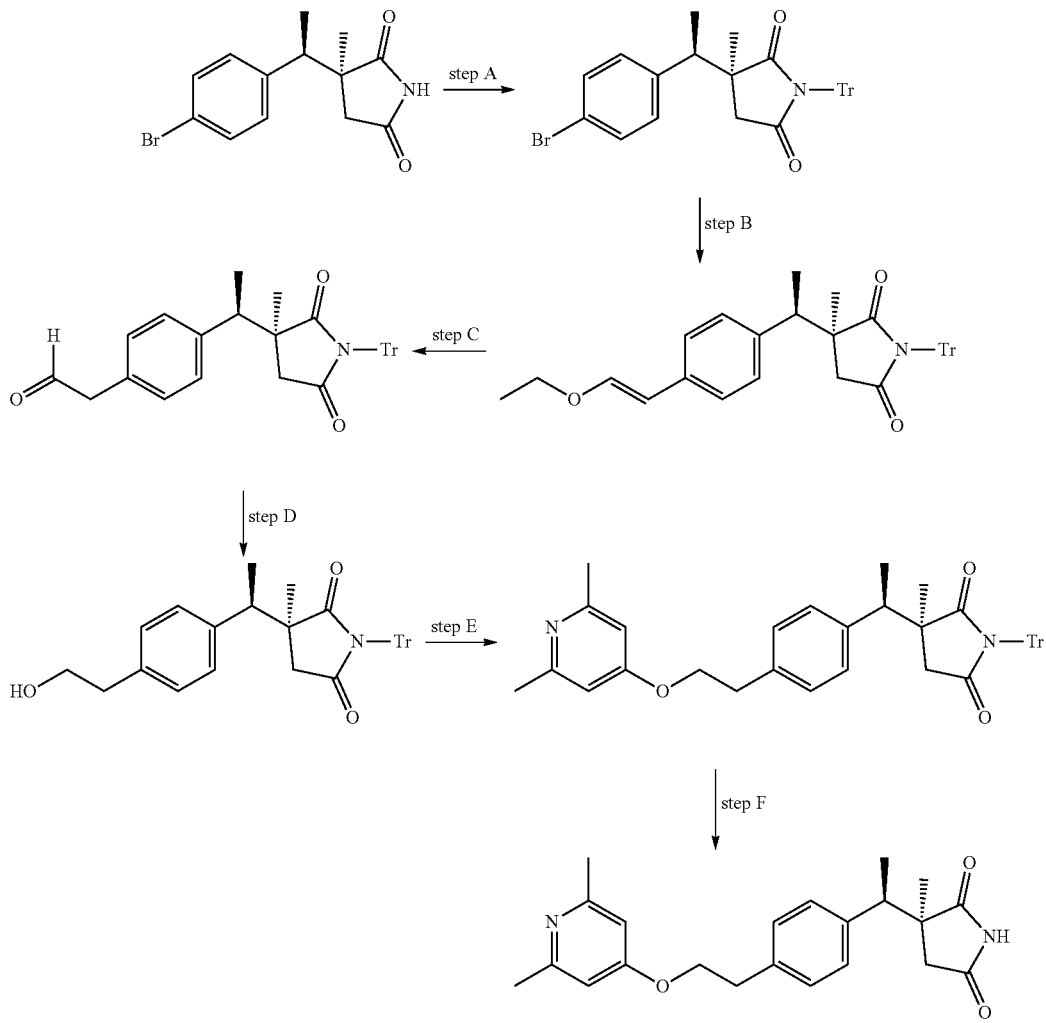

Scheme 2 depicts an alternative synthesis to (3S)-3-[(1R)-1-[4-[2-[(2,6-dimethyl-4-pyridyl)oxy]ethyl]phenyl]ethyl]-3-methyl-pyrrolidine-2,5-dione. In Scheme 2, step A, the succinimide nitrogen of (3S)-3-[(1R)-1-(4-bromophenyl)ethyl]-3-methyl-pyrrolidine-2,5-dione, the product of Scheme 1, step H, may be protected with a suitable protecting group, such as a triphenylmethyl group, under conditions well known in the art. For example, about 1 equivalent (3S)-3-[(1R)-1-(4-bromophenyl)ethyl]-3-methyl-pyrrolidine-2,5-dione may be dissolved in a suitable polar organic solvent, such as DMF or 1,4-dioxane, and treated with about 1.2 equivalents triphenylmethyl chloride and a suitable non-nucleophilic base, such as $Na_2CO_3$ or $Cs_2CO_3$, at about 0° C. for about 2 h. The product may be isolated by utilizing techniques well known in the art, such as filtration and recrystallization. For example, the reaction mixture may be diluted with water and the resulting solids collected by filtration. The filter cake may be reconstituted in a suitable polar organic solvent, such as MeOH or EtOH, heated to reflux, cooled to RT, and the subsequent solids may be collected by filtration and dried in a vacuum oven to provide (3S)-3-[(1R)-1-(4-bromophenyl)ethyl]-3-methyl-1-trityl-pyrrolidine-2,5-dione, the product of Scheme 2, step A.

In Scheme 2, step B, the vinyl ether may be prepared via a Suzuki coupling reaction with the appropriate vinyl borolane as is well known to the skilled artisan. For example, about 1 equivalent of (3S)-3-[(1R)-1-(4-bromophenyl)ethyl]-3-methyl-1-trityl-pyrrolidine-2,5-dione, the product of Scheme 2, step A, may be dissolved in a suitable degassed organic solvent, e.g., THF, DMF, 1,4-dioxane, or a mixture of these with water, in the presence of about 1.1 equivalents 2-[(E)-2-ethoxyvinyl]-4,4,5,5-tetramethyl-1,3,2-dioxaborolane, about 0.025-0.05 equivalents of a suitable palladium metal-ligand complex, e.g., 1,1'-bis(diphenylphosphino)ferrocene-palladium(II)dichloride dichloromethane complex, and about 3 equivalents of a suitable inorganic base, e.g., $Cs_2CO_3$. The resulting mixture may be heated to reflux under nitrogen for about 30 min. The product may be isolated by utilizing techniques well known in the art, such as extraction and recrystallization. For example, the reaction mixture may be diluted with water and extracted with a suitable organic solvent such as DCM, MTBE, $Et_2O$, or EtOAc. The organic extracts may be concentrated under reduced pressure, reconstituted in a suitable polar organic solvent, e.g., MeOH or EtOH, heated to reflux, and cooled to RT. The resulting solids may be collected by filtration and the filter cake dried under a stream of nitrogen to provide (3S)-3-[(1R)-1-[4-[(E)-2-ethoxyvinyl]phenyl]ethyl]-3-methyl-1-trityl-pyrrolidine-2,5-dione, the product of Scheme 2, step B.

Scheme 2, step C, depicts the hydrolysis of the vinyl ether to obtain the corresponding aldehyde, as is well described in the art. For example, about 1 equivalent of (3S)-3-[(1R)-1-[4-[(E)-2-ethoxyvinyl]phenyl]ethyl]-3-methyl-1-trityl-pyrrolidine-2,5-dione, the product of Scheme 2, step B, may be dissolved in a suitable polar organic solvent, e.g., acetone, and the resulting solution treated with an aqueous mineral acid, e.g., HCl. The mixture may be heated to about 60° C. for about 1 h. The product may be isolated utilizing techniques well known in the art, such as filtration. For example, the reaction mixture may slowly diluted with water, cooled to RT, and the resulting solid may be collected by filtration and dried under a stream of nitrogen to provide 2-[4-[(1R)-1-[(3S)-3-methyl-2,5-dioxo-1-trityl-pyrrolidin-3-yl]ethyl]phenyl]acetaldehyde, the product of Scheme 2, step C.

Scheme 2, step D, depicts the reduction of the aldehyde product of Scheme 2, step C, which may be reduced under an array of conditions well known in the art, including reduction with borohydrides. For example, about 1 equivalent of 2-[4-[(1R)-1-[(3S)-3-methyl-2,5-dioxo-1-trityl-pyrrolidin-3-yl]ethyl]phenyl]acetaldehyde may be dissolved in a suitable organic mixture, e.g., DCM/EtOH, and treated with about 1.5 equivalents of a suitable borohydride, e.g., NaBH$_4$, at about 0° C. The product may be isolated utilizing techniques well known in the art, such as extraction. For example, the reaction mixture may be quenched with water and extracted with an appropriate organic solvent, e.g., DCM, and the organic extract separated, dried over Na$_2$SO$_4$, filtered, and concentrated under reduced pressure, to obtain (3S)-3-[(1R)-1-[4-(2-hydroxyethyl)phenyl]ethyl]-3-methyl-1-trityl-pyrrolidine-2,5-dione, the product of Scheme 2, step D, of sufficient purity for additional use without further purification.

In Scheme 2, step E, arylation of (3S)-3-[(1R)-1-[4-(2-hydroxyethyl)phenyl]-ethyl]-3-methyl-1-trityl-pyrrolidine-2,5-dione, the product of scheme 2, step D, may be accomplished under conditions similar to those described in Scheme 1, step M, to provide (3S)-3-[(1R)-1-[4-[2-[(2,6-dimethyl-4-pyridyl)oxy]ethyl]phenyl]ethyl]-3-methyl-1-trityl-pyrrolidine-2,5-dione, the product of Scheme 2, step E.

Scheme 2, step F, depicts the deprotection of the succinimide nitrogen or (3S)-3-[(1R)-1-[4-[2-[(2,6-dimethyl-4-pyridyl)oxy]ethyl]phenyl]ethyl]-3-methyl-1-trityl-pyrrolidine-2,5-dione, the product of Scheme 2, step E, which may be accomplished under a variety of conditions well known in the art. For example, about 1 equivalent of (3S)-3-[(1R)-1-[4-[2-[(2,6-dimethyl-4-pyridyl)oxy]ethyl]phenyl]ethyl]-3-methyl-1-trityl-pyrrolidine-2,5-dione may be dissolved in a suitable organic solvent, e.g., DCM, and treated with an excess of an appropriate organic acid, e.g., TFA, at about 0° C. to RT for about 1-18 h. The product may be isolated by utilizing techniques well known in the art, such as extraction and chromatography. For example, the reaction mixture may be partitioned between a suitable organic solvent, e.g., MTBE, and an aqueous mineral base, e.g., NaOH. The layers may be separated, and the aqueous phase may be neutralized to pH~6 with a suitable aqueous mineral acid, e.g., HCl. The acidified mixture may be extracted with a suitable organic solvent, e.g., DCM or EtOAc, the layers may be separated, and the organic extracts may be dried over Na$_2$SO$_4$, filtered, and concentrated under reduced pressure. The resulting residue may be purified by flash chromatography on silica, eluting with a suitable organic solvent mixture, such as MeOH in DCM, to provide (3S)-3-[(1R)-1-[4-[2-[(2,6-dimethyl-4-pyridyl)oxy]ethyl]phenyl]ethyl]-3-methyl-pyrrolidine-2,5-dione, the product of Scheme 2, step F.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R- or S-configuration of the compound of the invention may be determined by standard techniques such as X-ray analysis and correlation with chiral-HPLC retention time.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10 ° C.; flow rate: 1.2 mL/min; Solvent A: 10 mM NH$_4$HCO$_3$ pH 9; Solvent B: ACN; wavelength: 214 nm.

Preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX® GEMINI®-NX, 5µ particle size columns with a 10×20 mm guard. Flow rate of 85 mL/min. Eluent is 10 mM ammonium bicarbonate (pH 10) in acetonitrile.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

Isopropyl (3S)-3-(4-bromophenyl)butanoate

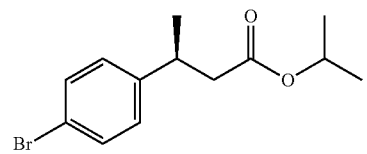 [SMILES: CC(C)OC(=O)C[C@H](C)c1ccc(Br)cc1]

Scheme 1, step A: To a deoxygenated solution of (4-bromophenyl)boronic acid (110 g, 547.73 mmol) in 1,4-dioxane (750 mL) under $N_2$ atmosphere is added bis(norbornadiene)rhodium(I) tetrafluoroborate (2 g, 5.13 mmol) followed by (R)-(+)-2,2'-bis(diphenylphosphino)-1,1'-binaphthyl (4.5 g, 7.2 mmol). The mixture is aged at room temperature for 1 hr before adding $H_2O$ (100 mL), TEA (70 mL, 502 mmol), and isopropyl (E)-but-2-enoate (65 g, 507.14 mmol). The resulting red solution is heated to 40° C. for 18 hr. The reaction mixture is concentrated under reduced pressure to half volume and diluted with 500 mL MTBE. The organic solution is washed with 500 mL water, dried over $Na_2SO_4$, filtered, and concentrated to dryness under reduced pressure. The crude product is purified by flash chromatography on silica, eluting with hexanes/EtOAc (gradient from 1:0 to 9:1). The pure chromatography fractions are combined and concentrated under reduced pressure to give the title compound (144 g, 94.6% yield, 94.5% ee). Major enantiomer $t_R$=2.20 min; minor enantiomer $t_R$=2.69 min (Chiral SFC Lux Amylose-2, 5% MeOH/$CO_2$, 5 mL/min, 225 nm). $^1$H NMR (DMSO-$d_6$): δ 1.05 (d, J=6.2 Hz, 3H), 1.10 (d, J=6.2 Hz, 3H), 1.19 (d, J=7.0 Hz, 3H), 2.48-2.59 (m, 2H), 3.08-3.19 (m, 1H), 4.74-4.84 (m, 1H), 7.20-7.24 (m, 2H), 7.44-7.48 (m, 2H).

Preparation 2

(3S)-3-(4-bromophenyl)butanoic acid

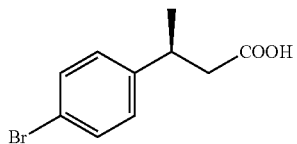

Scheme 1, step B: To a solution of isopropyl (3S)-3-(4-bromophenyl)butanoate (1042 g, 3471.0 mmol) in MeOH (8 L) is added 5 M aqueous NaOH (2 L) while stirring at RT. The reaction is heated to 50° C. under $N_2$ atmosphere for 40 min. After cooling down to 30° C., the reaction mixture is concentrated under reduced pressure and the residue is diluted with 2 L water. The resulting aqueous mixture is extracted once with DCM (~2 L). The aqueous layer is treated with ~1 kg of ice and acidified to pH~4 with conc. HCl (1 L) by slow addition over the course of 20 min. The cloudy aqueous layer is then extracted with DCM (~4 L). The organic layer is dried over $Na_2SO_4$, filtered, and concentrated under reduced pressure to a clear tan oil which solidified to an off-white solid. Heptane (~4 L) is added to the solid and the resulting mixture is heated to 45° C. for 2 hr upon which a solid precipitates. The solids are collected by filtration and washed with heptane (200-250 mL). The filtrate is concentrated to dryness under reduced pressure to give the title compound as an off-white solid (771 g, 91.4% yield, 99% ee). ES/MS (m/z): 241.0 (M-H). Major enantiomer $t_R$=2.35 min; minor enantiomer $t_R$=2.82 min (Chiral SFC Lux Amylose-2, 5% MeOH/$CO_2$, 5 mL/min, 225 nm). $^1$H NMR (DMSO-$d_6$): δ 1.19 (d, J=7.0 Hz, 3H), 2.48-2.52 (m, 2H), 3.07-3.17 (m, 1H), 7.20-7.25 (m, 2H), 7.44-7.49 (m, 2H), 12.08 (s, 1H). $[α]_D^{25}$+25.0° (c=1, MeOH).

Preparation 3 methyl (3S)-3-(4-bromophenyl)butanoate

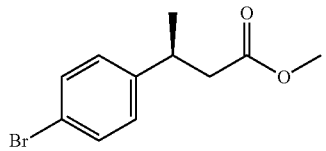

Scheme 1, step C: Concentrated $H_2O_4$ (45 mL, 802 mmol) is added to a solution of (3S)-3-(4-bromophenyl)butanoic acid (450 g, 1851.1 mmol) in MeOH (4.5 L). The mixture is heated at 65° C. for 2 h, cooled to RT, and concentrated under reduced pressure to a dry residue. The solid is diluted with MTBE (2.5 L) and $H_2O$ (2.5 L) and the resulting mixture is extracted with MTBE (2×2.5 L). The combined extracts are washed with $H_2O$ (2.5 L), dried over $MgSO_4$, filtered, and concentrated under reduced pressure to give the title compound as a light yellow oil (469.8 g, >99% yield) that may be used without further purification. ES/MS (m/z): 274.0 (M+$NH_4^+$). $^1$H NMR ($CDCl_3$): δ 1.27 (d, J=7.0 Hz, 3H), 2.50-2.62 (m, 2H), 3.20-3.30 (m, 1H), 3.61 (s, 3H), 7.07-7.12 (m, 2H), 7.39-7.43 (m, 2H).

Preparation 4

(3S,2R)-methyl 3-(4-bromophenyl)-2-methylbutanoate and (3S,2S)-methyl 3-(4-bromophenyl)-2-methylbutanoate

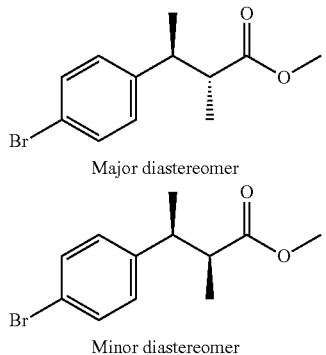

Scheme 1, step D: A 2.5 M solution of n-BuLi in hexanes (1250 mL) is added drop wise to a solution of DIPEA (444 mL, 3150 mmol) in anhydrous THF (2.3 L) at −40° C. over 30 min. After 30 min, a solution of methyl (3S)-3-(4-bromophenyl)butanoate (468.90 g, 1750.7 mmol) in anhydrous THF (3.3 L) is added over 40 min, and the reaction mixture is aged for 40 min at −40° C. $CH_3I$ (176 mL, 2798 mmol) is added over 30 min and the mixture is stirred for 15 min at −40° C. The reaction mixture is quenched slowly at −40° C. with MeOH (283 mL) followed by $H_2O$ (2.5 L) and the mixture is allowed to warm to RT. The reaction mixture is diluted with $H_2O$ (2.5 L) and the resulting layers are separated. The aqueous layer is additionally extracted with MTBE (7.5 L) and the combined organic extracts are washed sequentially with H₂O (3 L) and saturated aqueous NaCl (2.5 L). The organic extracts are dried over MgS₄, filtered, and concentrated under reduced pressure to give the title compound as a mixture of diastereomers (7:3) as a light brown oil (489 g, 93% yield) that may be used without further purification. Major diastereomer $t_R$=1.29 min; minor diastereomer $t_R$=1.32 min (XBRIDGE® C18 column, 3.5µ, 2.1×50 mm, 1.2 mL/min, 50° C., 10-95% 10 mM NH₄CO₃ (pH 10) in ACN). ES/MS (m/z for $^{79}$Br/$^{81}$Br): 288.0, 290.0 (M+NH₄⁺).

Preparation 5

4-(tert-butyl) 1-methyl (S)-2-((R)-1-(4-bromophenyl)ethyl)-2-methylsuccinate and 4-(tert-butyl) 1-methyl (R)-2-((R)-1-(4-bromophenyl)ethyl)-2-methylsuccinate

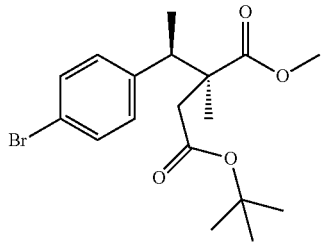

Major diastereomer

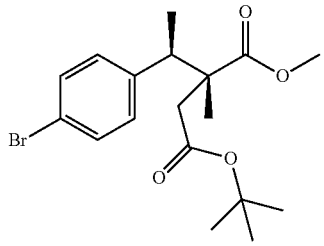

Minor diastereomer

Scheme 1, step E: A 2.5 M solution of n-BuLi in hexanes (1150 mL, 2900 mmol) is added over 20 min to a solution of DIPEA (410 mL, 2910 mmol) in anhydrous THF (3 L) at −40° C. The resulting mixture is stirred at −40° C. for 30 min, and a solution of a mixture of diastereomers methyl (2R/S,3S)-3-(4-bromophenyl)-2-methyl-butanoate (488.00 g, 1619.8 mmol) in anhydrous THF (3 L) is added over a period of 1 hr. The reaction mixture is aged for 45 min at −40° C., and a solution of tert-butyl 2-bromoacetate (391 mL, 2596 mmol) in anhydrous THF (250 mL) is added over 30 min. The resulting mixture is stirred for an additional 30 min at −40° C. MeOH (250 mL) is added followed by H₂O (2.5 L), and the resulting mixture is allowed to warm to RT. The mixture is diluted with H₂O (2.5 L) and the resulting layers are separated. The aqueous layer is extracted with MTBE (5 L), and the organic extract is washed sequentially with H₂O (5 L) followed by saturated aqueous NaCl (2.5 L), dried over MgSO₄, filtered, and concentrated under reduced pressure to give the title compound as a mixture of diastereomers as a thick brown oil (786 g, 87% yield) that may be used without further purification. Major diastereomer $t_R$=1.51 min; minor diastereomer $t_R$=1.53 min (XBRIDGE® C18 column, 3.5µ, 2.1×50 mm, 1.2 mL/min, 50° C., 10-95% 10 mM NH₄CO₃ (pH 10) in ACN). ES/MS (m/z for $^{79}$Br/$^{81}$Br): 328.8, 330.8 (M-tBu+H).

Preparation 6

(3S,4R)-4-(4-bromophenyl)-3-(methoxycarbonyl)-3-methylpentanoic acid and (3R,4R)-4-(4-bromophenyl)-3-(methoxycarbonyl)-3-methylpentanoic acid

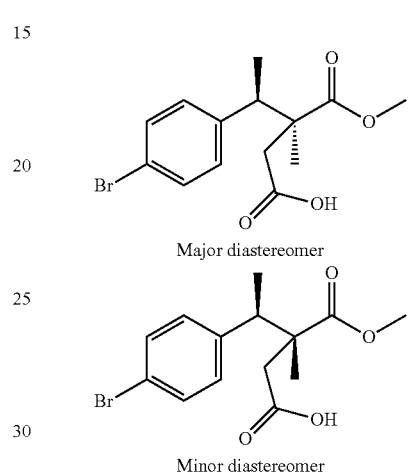

Major diastereomer

Minor diastereomer

Scheme 1, step F: A solution of a mixture of diastereomers 4-(tert-butyl) 1-methyl (R/S)-2-((R)-1-(4-bromophenyl)ethyl)-2-methylsuccinate (785 g, 1406 mmol) in DCM (6 L) is treated with TFA (1.06 L) and stirred at RT for 18 hr. The reaction mixture is washed sequentially with H₂O (2×5 L) and saturated aqueous NaCl (5 L). The organic extracts are dried over MgSO₄, filtered, and concentrated under reduced pressure to give the title compound as a mixture of diastereomers (8:2) as a dark brown gum (604 g, 91% yield) that may be used without further purification. ES/MS (m/z for $^{79}$Br/$^{81}$Br): 329.0, 331.0 (M+H).

Preparation 7 methyl (2S)-4-amino-2-[(1R)-1-(4-bromophenyl)ethyl]-2-methyl-4-oxo-butanoate and methyl (2R)-4-amino-2-[(1R)-1-(4-bromophenyl)ethyl]-2-methyl-4-oxo-butanoate

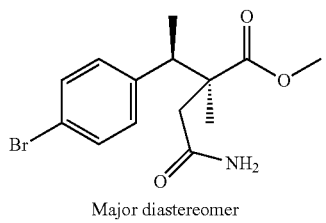

Major diastereomer

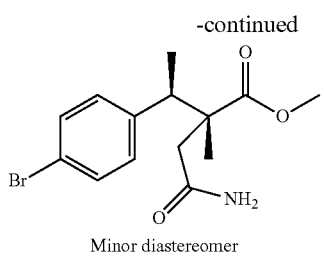

Minor diastereomer

Scheme 1, step G: To a mixture of diastereomers (3R/S, 4R)-4-(4-bromophenyl)-3-methoxycarbonyl-3-methylpentanoic acid (603 g, 1282 mmol) and TEA (550 mL, 3870 mmol) in anhydrous DMF (4 L) at 0° C. is added HATU (597 g, 1538.69 mmol) over 15 min. The reaction mixture is aged at RT for 2 hr. A solution of 7 M $NH_3$/MeOH (1.83 L) is added over 30 min at 10° C., and the resulting mixture is warmed to RT and stirred for 1 h. The reaction mixture is cooled to 10° C. and then diluted slowly with DCM (5 L) followed by $H_2O$ (5 L). The resulting layers are separated, and the aqueous layer is additionally extracted with DCM (2.5 L). The combined extracts are washed sequentially with $H_2O$ (5L) and saturated aqueous NaCl (5 L), dried over $MgSO_4$, filtered, and concentrated under reduced pressure to give the title compound as a mixture of diastereomers (8:2) as a dark gum (520 g, 87% yield) that may be used without further purification. Major diastereomer $t_R$=0.97 min; minor diastereomer $t_R$=0.99 min (XBRIDGE® C18 column, 3.5 m, 2.1×50 mm, 1.2 mL/min, 50° C., 10-95% 10 mM $NH_4CO_3$ (pH 10) in ACN). ES/MS (m/z for $^{79}Br/^{81}Br$) 328.0/330.0 (M+H/M+H+2).

Preparation 8

(3S)-3-[(1R)-1-(4-bromophenyl)ethyl]-3-methyl-pyrrolidine-2,5-dione and (3R)-3-[(1R)-1-(4-bromophenyl)ethyl]-3-methyl-pyrrolidine-2,5-dione

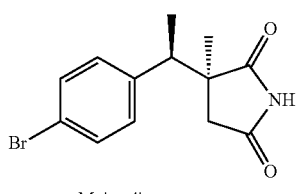

Major diastereomer

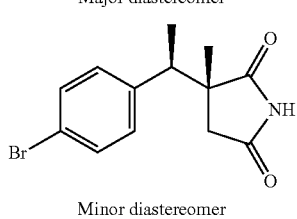

Minor diastereomer

Scheme 1, step H: To a mixture of diastereomers methyl (2R/S)-4-amino-2-[(1R)-1-(4-bromophenyl)ethyl]-2-methyl-4-oxo-butanoate (519 g, 1107 mmol) dissolved in THF (4.2 L) and $H_2O$ (4.2 L) is added $Na_2CO_3$ (293 g, 2764.46 mmol) and the mixture is heated at 60° C. for 2hr. The reaction is cooled to RT and extracted with EtOAc (2.5 L). The organic layer is washed with $H_2O$ (3 L). The resulting aqueous extract is extracted with EtOAc (5 L) and the combined organic extracts are dried over $MgSO_4$, filtered, and concentrated under reduced pressure to give a crude mixture of the two diastereomers that are separated by SFC [Column: AS-H, 150×50 mm; 10% EtOH (0.2% DEMA), 340 g/min; BPR 150 bar; injection volume: 4 ml; 220 nm]. (3R)-3-[(1R)-1-(4-bromophenyl)ethyl]-3-methyl-pyrrolidine-2,5-dione: first eluting compound (43.8 g, 11%). $^1$H NMR ($CDCl_3$): δ 1.33 (d, J=7.2 Hz, 3H), 1.40 (s, 3H), 2.34 (d, J=18.4 Hz, 1H), 2.80 (, J=18.4 Hz, 1H), 3.23 (q, J=7.2 Hz, 1H), 7.07 (d, 2H), 7.40 (d, 2H), 7.54 (br-s, 1H). ES/MS (m/z for $^{79}Br/^{81}Br$): 313.0, 315.0 (M+H). (3S)-3-[(1R)-1-(4-bromophenyl)ethyl]-3-methyl-pyrrolidine-2,5-dione: second eluting compound (241.8 g, 55%). $^1$H NMR ($CDCl_3$): δ 1.23 (s, 3H), 1.30 (d, J=7.1 Hz, 3H), 2.21 (d, J=18.4 Hz, 1H), 2.96 (d, J=18.4 Hz, 1H), 3.14 (q, J=7.1 Hz, 1H), 7.04-7.09 (m, 2H), 7.42-7.48 (m, 2H), 8.09 (br-s, 1H). ES/MS (m/z for $^{79}Br/^{81}Br$): 313.0, 315.0 (M+H).

Preparation 9

(3 S)-3-[(1R)-1-(4-bromophenyl)ethyl]-1-[(4-methoxyphenyl)methyl]-3-methyl-pyrrolidine-2,5-dione

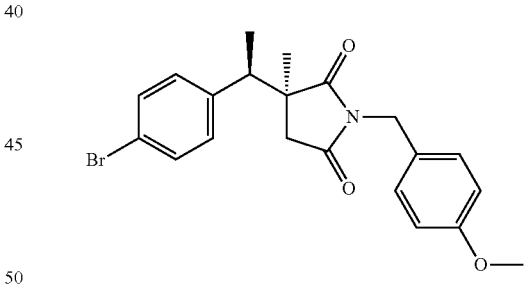

Scheme 1, step I: In a round bottom flask, with stirrer, under nitrogen, (3S)-3-[(1R)-1-(4-bromophenyl)ethyl]-3-methyl-pyrrolidine-2,5-dione (15.0 g, 50.6 mmol) is added to DMF (169 mL). $Cs_2CO_3$ (16.5 g, 50.6 mmol) followed by 1-(chloromethyl)-4-methoxy-benzene (6.9 mL, 50.6 mmol) are added, and the reaction is allowed to stir for 2 hr at 40° C. The reaction is poured onto saturated aqueous $NH_4Cl$ (ca. 400 mL), and the resulting mixture is extracted with EtOAc (2×300 mL). The organic layer is separated, dried over $MgSO_4$, filtered, and concentrated under reduced pressure. The crude product is purified by normal phase flash chromatography, eluting with 0-80% EtOAc in hexanes, to obtain the title compound as a white crystalline solid (14.9 g, 64% yield) after solvent removal. ES/MS (m/z $^{79}Br/^{81}Br$): 416.0, 418.0 (M+H).

Preparation 10 tert-butyl 2-[4-[(1R)-1-[(3S)-1-[(4-methoxyphenyl)methyl]-3-methyl-2,5-dioxo-pyrrolidin-3-yl]ethyl]phenyl]acetate

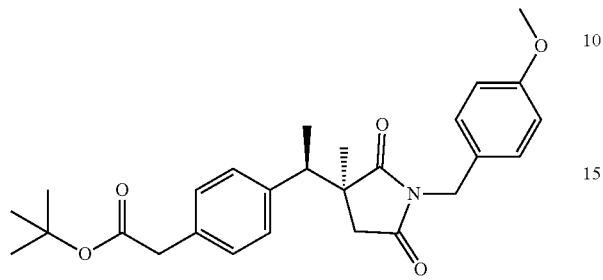

Scheme 1, step J: (3S)-3-[(1R)-1-(4-Bromophenyl)ethyl]-1-[(4-methoxyphenyl)methyl]-3-methyl-pyrrolidine-2,5-dione (14.9 g, 35.9 mmol) is added to a round bottom flask, with stirrer, and air condenser under nitrogen, containing dioxane (359 mL) and bis(tri-tert-butylphosphine)palladium (0) (1.9 g, 3.6 mmol). The mixture is vacuum/nitrogen purged three times and a 0.5 M solution of 2-tert-butoxy-2-oxoethylzinc chloride in Et$_2$O (140 mL, 71.7 mmol) is added dropwise over 10 minutes. Upon full addition, the mixture is heated to 60° C. After 7 h, additional bis(tri-tert-butylphosphine)palladium(0) (0.9 g, 1.8 mmol) is added; the mixture is kept at 60° C. for 30 min and cooled to RT. The reaction mixture is poured onto saturated aqueous NH$_4$Cl (500 mL), and the resulting mixture is extracted with Et$_2$O (2×300 mL). The organic layers are combined, dried over MgSO$_4$, filtered, and concentrated under reduced pressure. The crude product is purified by normal phase flash chromatography, eluting with 0-100% EtOAc in hexanes, to give the title compound as a light yellow oil (14.6 g, 90% yield) after solvent removal. ES/MS (m/z): 474.0 (M+H).

Preparation 11

2-[4-[(1R)-1-[(3S)-1-[(4-methoxyphenyl)methyl]-3-methyl-2,5-dioxo-pyrrolidin-3-yl]ethyl]phenyl]acetic acid

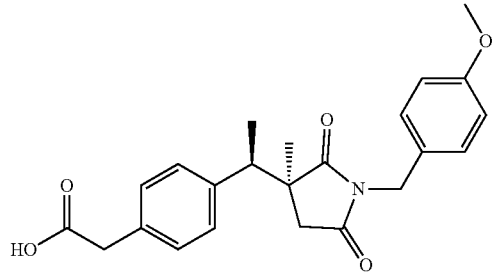 [SMILES: COc1ccc(CN2C(=O)C[C@@](C)([C@H](C)c3ccc(CC(=O)O)cc3)C2=O)cc1]

Scheme 1, step K: tert-Butyl 2-[4-[(1R)-1-[(3S)-1-[(4-methoxyphenyl)methyl]-3-methyl-2,5-dioxo-pyrrolidin-3-yl]ethyl]phenyl]acetate (14.58 g, 32.29 mmol) is added to a round bottom flask, with stirrer, under nitrogen, containing DCM (129 mL). TFA (32.3 mL) is added and the resulting mixture is stirred at RT for 2 h. the reaction mixture is concentrated under reduced pressure, diluted with saturated aqueous NaCl (300 mL), and extracted with CHCl$_3$ (2×150 mL). The organic extracts are combined, dried over MgSO$_4$, filtered, and concentrated under reduced pressure to give the title compound as an orange oil (13.6 g, 100% yield), suitable for use without additional purification. ES/MS (m/z): 418.0 (M+H).

Preparation 12

(3S)-3-[(1R)-1-[4-(2-hydroxyethyl)phenyl]ethyl]-1-[(4-methoxyphenyl)methyl]-3-methyl-pyrrolidine-2,5-dione

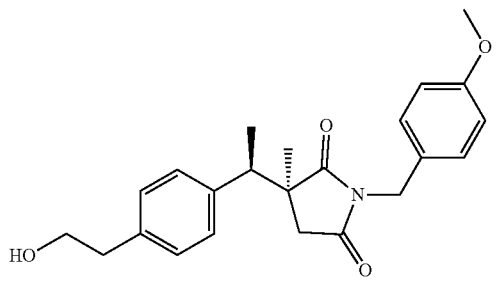 [SMILES: COc1ccc(CN2C(=O)C[C@@](C)([C@H](C)c3ccc(CCO)cc3)C2=O)cc1]

Scheme 1, step L: 2-[4-[(1R)-1-[(3S)-1-[(4-Methoxyphenyl)methyl]-3-methyl-2,5-dioxo-pyrrolidin-3-yl]ethyl]phenyl]acetic acid (13.6 g, 34.3 mmol) is added to THF (343 mL) in a round bottom flask, with stirrer, under nitrogen. Borane dimethyl sulfide complex (7.0 mL, 75.4 mmol) is added, and the resulting mixture is stirred at RT for 2 h. MeOH (10 mL) is cautiously added, resulting in effervescence, and the resulting mixture stirred for 1 h. The reaction mixture is poured into saturated aqueous NaHCO$_3$ (500 mL) and the mixture is extracted with EtOAc (2×300 mL). The organic extracts are combined, dried over MgSO$_4$, filtered, and concentrated under reduced pressure. The resulting light yellow oil is purified by normal phase flash chromatography, eluting with 0-100% EtOAc in hexanes, to give the title compound as a light yellow oil (11.5 g, 88% yield) after solvent removal. ES/MS (m/z): 382.0/404.0 (M+H, M+Na).

Preparation 13

Pd$_2$dba$_3$-tBuBrettPhos-Cs$_2$CO$_3$ Etherification Mix

To a round bottom flask, with stirrer, under nitrogen, is added Cs$_2$CO$_3$ (74.5 g, 229 mmol), tris(dibenzylideneacetone)dipalladium(0) (2.16 g, 2.29 mmol), 2-(di-tert-butylphosphino)-2',4',6'-triisopropyl-3,6-dimethoxy-1,1'-biphenyl (4.57 g, 9.15 mmol), and toluene (457 mL). The resulting dark purple solution is vacuum/nitrogen purged three times, and heated to 80° C. for 1 h. The reaction is concentrated under reduced pressure and the resulting residue is ground to a fine powder with mortar and pestle to give the title compound as a brick-red solid, which is stored under nitrogen (79.0 g, 93% yield). ES/MS (m/z): 491.0/501.0.

Preparation 14

(3S)-3-[(1R)-1-[4-[2-[(2,6-dimethyl-4-pyridyl)oxy]ethyl]phenyl]ethyl]-1-[(4-methoxyphenyl)methyl]-3-methyl-pyrrolidine-2,5-dione

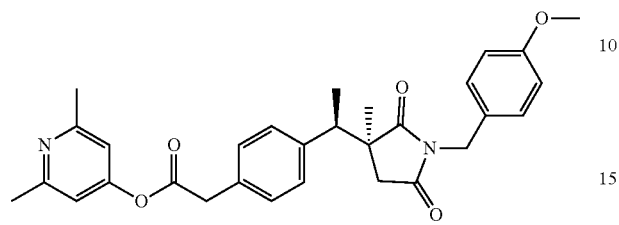

Scheme 1, step M: (3S)-3-[(1R)-1-[4-(2-Hydroxyethyl)phenyl]ethyl]-1-[(4-methoxyphenyl)methyl]-3-methyl-pyrrolidine-2,5-dione (530 mg, 1.3 mmol), 4-bromo-2,6-dimethyl-pyridine (0.5 g, 2.5 mmol), Pd$_2$dba$_3$-tBuBrettPhos-Cs$_2$CO3 Etherification Mix (0.7 g,) and toluene (13 mL) are added to a microwave vial. The resulting mixture is sealed, nitrogen/vacuum purged 3 times, and heated in an oil bath at 85° C. for 4 h. Additional Pd$_2$dba$_3$-tBuBrettPhos-Cs$_2$CO$_3$ Etherification Mix (0.7 g) is added, and the mixture is heated at 85° C. for 20 h. The reaction mixture is cooled to RT, poured into saturated aqueous NH$_4$Cl (50 mL), and the resulting mixture is extracted with EtOAc (2×60 mL). The organic extracts are dried over MgSO$_4$, filtered, and concentrated under reduced pressure. The resulting orange oil is purified by normal phase flash purification, eluting with 0-100% EtOAc in hexanes, to give the title compound as a yellow oil (0.6 g, 54% yield) after solvent removal. ES/MS (m/z): 487.0 (M+H).

Preparation 15

(3S)-3-[(1R)-1-(4-bromophenyl)ethyl]-3-methyl-1-trityl-pyrrolidine-2,5-dione

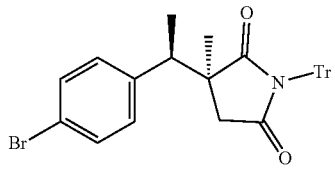

Scheme 2, step A: (3S)-3-[(1R)-1-(4-Bromopheny)ethyl]-3-methyl-pyrrolidine-2,5-dione (25.0 g, 84.4 mmol) is dissolved in DMF (250 mL) in a 3-necked flask under nitrogen at RT. Triphenylmethyl chloride (29.0 g, 110.9 mmol) is added, and the reaction mixture is cooled to about 0° C. Cs$_2$CO$_3$ (41.0 g, 125.8 mmol) is added portion wise over about 5 min, and the resulting mixture is allowed to warm to RT over about 2 h. The reaction mixture is cooled to about 5° C., and water (250 mL) is added dropwise over 20 min. The resulting solids are collected by filtration, the filter cake is washed with water and dried under a stream of nitrogen, and additionally dried in a vacuum oven at 50° C. overnight. The solids are suspended in MeOH (500 mL) and the mixture is heated to reflux for a few min. The mixture is cooled to RT, the resulting solids are collected by filtration and dried under a stream of nitrogen to obtain the title compound. The solids are further dried in a vacuum oven at 50° C. to obtain the title compound (43.5 g, 95.7% yield) as a white solid. $^1$H NMR (399.80 MHz, CDCl$_3$): 7.43-7.40 (m, 8H), 7.29-7.26 (m, 7H), 7.23 (d, J=8.4 Hz, 2), 6.99 (d, J=8.4 Hz, 2H), 2.87 (d, J=17.9 Hz, 1H), 2.17 (d, J=17.9 Hz, 1H), 1.13 (s, 3H), 0.96 (d, J=7.0 Hz, 3H).

Preparation 16

(3S)-3-[(1R)-1-[4-[(E)-2-ethoxyvinyl]phenyl]ethyl]-3-methyl-1-trityl-pyrrolidine-2,5-dione

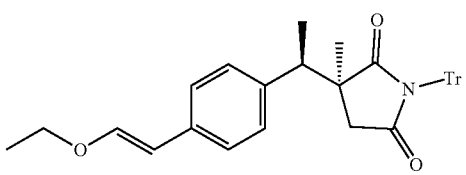

Scheme 2, step B: (3S)-3-[(1R)-1-(4-bromophenyl)ethyl]-3-methyl-1-trityl-pyrrolidine-2,5-dione (43.5 g, 80.8 mmol), 2-[(E)-2-ethoxyvinyl]-4,4,5,5-tetramethyl-1,3,2-dioxaborolane (17.6 g, 88.8 mmol), Cs2CO3 (80.0 g, 245.5 mmol) 1,4-dioxane (450 mL) and water (90 mL) are added to a 3-necked 2 L flask, with mechanical stirring, under nitrogen. The reaction mixture is purged with nitrogen/vacuum, 1,1'-bis(diphenylphosphino)ferrocene-palladium(II)dichloride-DCM complex (1.7 g, 2.0 mmol) is added, and the reaction mixture is heated to reflux for about 30 min. The reaction mixture is cooled to RT, poured into 500 mL water/500 mL MTBE, and the resulting layers are separated. The organic layer is dried over Na$_2$SO$_4$, filtered, concentrated under reduced pressure, and the resulting residue is reconstituted in DCM (250 mL) and again evaporated under reduced pressure. The resulting residue is transferred to a 3-necked round bottom flask, MeOH (750 mL) is added, and the mixture is heated to a gentle reflux. Water (250 mL) is added dropwise over 15 min, and the mixture is cooled to RT. The resulting solids are collected by filtration, washed with 3:1 MeOH/water (100 mL), and dried under a stream of nitrogen to obtain the title compound (39.2 g, 91.6% yield) as a light green solid. ES/MS (m/z): 530.2 (M+H).

Preparation 17

2-[4-[(1R)-1-[(3S)-3-methyl-2,5-dioxo-1-trityl-pyrrolidin-3-yl]ethyl]phenyl]acetaldehyde

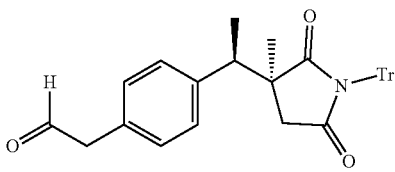

Scheme 2, step C: (3S)-3-[(1R)-1-[4-[(E)-2-ethoxyvinyl]phenyl]ethyl]-3-methyl-1-trityl-pyrrolidine-2,5-dione (39.2 g, 74.0 mmol) is dissolved in acetone (400 mL) and a 2 M aqueous solution of HCl (156 mL) is added at RT under nitrogen. The mixture is heated to 60° C. for 2 h. Water (250 mL) is added dropwise over 15 min to the 60° C. solution and the reaction mixture is cooled to RT. The resulting solids are collected by filtration, washed with water (100 mL), dried under a stream of nitrogen, and additionally dried in a vacuum oven at 45-50° C. to obtain the title compound (36.5 g, 98% yield) as a brown solid, suitable for additional use without further purification. ¹H NMR (399.80 MHz, CDCl₃): 9.76 (t, J=2.3 Hz, 1H), 7.43-7.40 (m, 7H), 7.29-7.22 (m, 12H), 3.69 (d, J=2.2 Hz, 2H), 2.94 (d, J=18.0 Hz, 1H), 2.17 (d, J=18.0 Hz, 1H), 1.13 (s, 3H), 0.99 (d, J=7.0 Hz, 3H).

Preparation 18

(3S)-3-[(1R)-1-[4-(2-hydroxyethyl)phenyl]ethyl]-3-methyl-1-trityl-pyrrolidine-2,5-dione

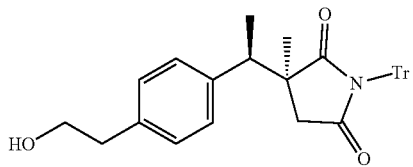

Scheme 2, step D: 2-[4-[(1R)-1-[(3S)-3-Methyl-2,5-dioxo-1-trityl-pyrrolidin-3-yl]ethyl]phenyl]acetaldehyde (36.5 g, 72.7 mmol) is dissolved in DCM (180 mL) and EtOH (180 mL) is added. The reaction mixture is cooled to about 0° C. and NaBH₄ (4.1 g, 110 mmol) is added portion wise over about 10 min. After stirring at about 0 oC for 30 min, water (400 mL) is slowly added to the reaction mixture; the mixture is further diluted with DCM (200 mL) and the layers are separated. The organic extract is dried over Na₂SO₄, filtered, concentrated under reduced pressure, and the resulting residue further dried in a vacuum oven at 50° C. to obtain the title compound (34.9 g, 95% yield) as a dark grey solid, suitable for use without additional purification. ES/MS (m/z): 521.0 (M+NH₄⁺).

Preparation 19

(3S)-3-[(1R)-1-[4-[2-[(2,6-dimethyl-4-pyridyl)oxy]ethyl]phenyl]ethyl]-3-methyl-1-trityl-pyrrolidine-2,5-dione

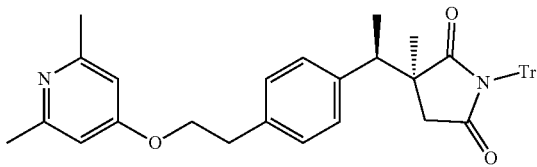

Scheme 2, step E: (3S)-3-[(1R)-1-[4-(2-hydroxyethyl)phenyl]ethyl]-3-methyl-1-trityl-pyrrolidine-2,5-dione (29.5 g, 58.6 mmol) is dissolved in toluene (300 mL). 4-Bromo-2,6-dimethyl-pyridine (17.0 g, 91.4 mmol) and Cs₂CO₃ (57.0 g, 175.0 mmol) are added and the mixture is thoroughly degassed. 2-(di-tert-Butylphosphino)-2',4',6'-triisopropyl-3,6-dimethoxy-1,1'-biphenyl (2.1 g, 4.2 mmol) and tris(dibenzylideneacetone) dipalladium(0) (2 g, 2.1 mmol) are added, and the resulting mixture is heated at 100° C. overnight. Additional 4-bromo-2,6-dimethyl-pyridine (5.3 g), 2-(di-tert-butylphosphino)-2',4',6'-triisopropyl-3,6-dimethoxy-1,1'-biphenyl (1.0 g), and tris(dibenzylideneacetone) dipalladium(0) (1.0 g) are added, the mixture is purged with nitrogen, and heated at 100° C. for 4 h. The reaction mixture is cooled to RT, diluted with EtOAc (300 mL) and water (500 mL), and the phases are separated. The organic extract is washed with saturated aqueous NaCl, dried over Na₂SO₄, filtered, and concentrated under reduced pressure. The crude product is purified by flash chromatography on silica, eluting with 25-50% EtOAc in DCM to obtain the title compound (11.0 g, 31% yield) after solvent evaporation and vacuum drying at 50° C. ¹H NMR (399.80 MHz, CDCl₃): 7.42-7.40 (m, 5H), 7.28-7.25 (m, 8H), 7.22-7.18 (m, 4H), 7.08 (d, J=8.1 Hz, 2H), 6.51 (s, 2H), 4.21-4.17 (m, 2H), 3.10-3.07 (m, 2H), 2.94 (d, J=18.0 Hz, 1H), 2.49 (s, 6H), 2.16 (d, J=18.0 Hz, 1H), 1.12 (s, 3H), 0.99 (d, J=7.1 Hz, 3H).

Example 1

(3S)-3-[(1R)-1-[4-[2-[(2,6-dimethyl-4-pyridyl)oxy]ethyl]phenyl]ethyl]-3-methyl-pyrrolidine-2,5-dione

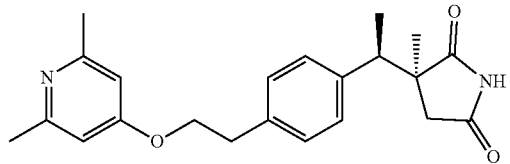 [SMILES: Cc1cc(OCCc2ccc([C@@H](C)[C@]3(C)CC(=O)NC3=O)cc2)cc(C)n1]

Scheme 1, step N: (3S)-3-[(1R)-1-[4-[2-[(2,6-Dimethyl-4-pyridyl)oxy]ethyl]phenyl]ethyl]-1-[(4-methoxyphenyl)methyl]-3-methyl-pyrrolidine-2,5-dione (578.0 mg, 1.2 mmol) is added to ACN (17 mL) and water (17 mL) in a round bottom flask and ceric ammonium nitrate (2.6 g, 4.8 mmol) is added. After stirring at RT for 2 h, an aqueous solution of 2M NaOH (11.89 mL, 23.8 mmol) is added, and the resulting mixture is stirred at RT for an additional 30 min. The reaction mixture is acidified to pH~3 with aqueous 2M HCl (5 mL), diluted with 2:1 CHCl₃/EtOH (100 mL), filtered through a bed of diatomaceous earth, and the organic phases are separated. The combined organic phases are dried over MgSO₄, filtered, and concentrated under reduced pressure to give a dark brown oil. The crude product is purified by preparative reverse phase chromatography (Column: PHENOMENEX® KINETEX® EVO C18, column length 100×30 mm, 5μ, 100 Å with 15×30 mm EVO guard using inline heater at 50° C.; solvents: aqueous 10 mM NH₄HCO₃ pH 10/5% MeOH (Solvent A) and ACN (Solvent B); gradient: 0-1 min hold at 13% solvent B, 1-8 min gradient from 13% to 48% solvent B, 8-8.1 min ramp from 48% to 100% solvent B, 8.1-10 min hold at 100% solvent B) to give the title compound as a brown oil (326.4 mg, 75% yield) after solvent evaporation. ES/MS (m/z): 367.0 (M+H). [α]$_D^{20}$=−40.393° (C=0.2, MeOH)

Alternative Procedure for Example 1

Scheme 2, step F: (3S)-3-[(1R)-1-[4-[2-[(2,6-Dimethyl-4-pyridyl)oxy]-ethyl]phenyl]ethyl]-3-methyl-1-trityl-pyrrolidine-2,5-dione (20.2 g, 33 mmol) is dissolved in DCM (100 ml) and the mixture is cooled to 0° C. in an ice bath. TFA (100 mL) is added dropwise over about 10 min; after complete addition, the reaction mixture is warmed to RT and stirred overnight. The reaction mixture is concentrated under reduced pressure and the resulting residue is partitioned between MTBE (300 mL)m and 2 N aqueous NaOH (300 mL). The layers are separated, the aqueous layer is acidified to pH~6 with conc aqueous HCl (ca. 25 mL), and extracted with DCM (2×250 mL). The organic extracts are combined, dried over $Na_2SO_4$, filtered, and the filtrate is concentrated under reduced pressure. The crude product is purified by flash chromatography on silica, eluting with 5-10% MeOH in DCM, to isolate 2 peaks.

The first (minor) peak is identified by $^1$H NMR as the freebase of the title compound. $^1$H NMR (399.80 MHz, $CDCl_3$): 8.18-8.15 (m, 1H), 7.24 (d, J=8.1 Hz, 2H), 7.17 (d, J=8.1 Hz, 2H), 6.52 (s, 2H), 4.21 (t, J=6.9 Hz, 2H), 3.09 (t, J=6.9 Hz, 2H), 3.03 (d, J=18.4 Hz, 1H), 2.49 (s, 6H), 2.23 (d, J=18.4 Hz, 1H), 1.34 (d, J=7.1 Hz, 3H), 1.27 (s, 3H).

The second (major) peak is identified by $^1$H and $^{19}$F nmr as the TFA salt of the title compound. $^1$H NMR (399.80 MHz, $CDCl_3$): 8.06 (s, 1H), 7.23 (d, J=8.3 Hz, 2H), 7.18 (d, J=8.2 Hz, 2H), 6.77 (s, 2H), 4.36 (t, J=6.8 Hz, 2H), 3.18 (t, J=6.8 Hz, 2H), 2.98 (d, J=18.4 Hz, 1H), 2.73 (s, 6H), 2.24 (d, J=18.3 Hz, 1H), 1.36 (d, J=7.1 Hz, 3H), 1.28 (s, 3H). $^{19}$F NMR (399.80 MHz, $CDCl_3$): −75.9.

The freebase and TFA salt fractions are combined, concentrated under reduced pressure, and the resulting residue is dissolved in EtOAc (250 mL) and washed with saturated aqueous $NaHCO_3$ (250 mL). The organic extract is dried over $Na_2SO_4$, filtered, concentrated under reduced pressure, and dried in a vacuum oven at 50° C. overnight to obtain the title compound (6.58 g, 54% yield) as an off-white solid. ES/MS (m/z): 367.0 (M+H). $^1$H NMR (399.80 MHz, $CDCl_3$): 8.18-8.15 (m, 1H), 7.24 (d, J=8.1 Hz, 2H), 7.17 (d, J=8.1 Hz, 2H), 6.52 (s, 2H), 4.21 (t, J=6.9 Hz, 2H), 3.09 (t, J=6.9 Hz, 2H), 3.03 (d, J=18.4 Hz, 1H), 2.49 (s, 6H), 2.23 (d, J=18.4 Hz, 1H), 1.34 (d, J=7.1 Hz, 3H), 1.27 (s, 3H).

Example 1A (3S)-3-[(1R)-1-[4-[2-[(2,6-dimethyl-4-pyridyl)oxy]ethyl]phenyl]ethyl]-3-methyl-pyrrolidine-2,5-dione mesylate

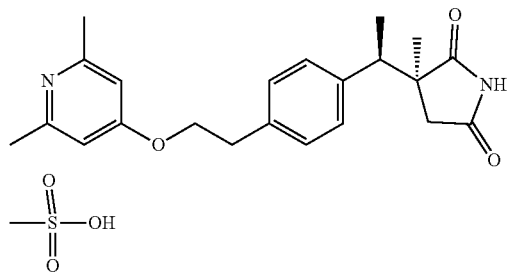

(3S)-3-[(1R)-1-[4-[2-[(2,6-dimethyl-4-pyridyl)oxy]ethyl]phenyl]ethyl]-3-methyl-pyrrolidine-2,5-dione (1.0 g, 2.7 mmol) is dissolved in acetone (10 mL) while stirring at 1000 rpm at 60° C. Methanesulfonic acid (200 μL) diluted in 4 mL of acetone is added dropwise to the slurry, and the mixture becomes a slurry of off-white solid under a yellow supernatant. The mixture is stirred at 60° C./1000 rpm for 10 min, heating is shut off, and the mixture is cooled to RT. The off-white solid is isolated by vacuum filtration. The resulting filter cake of solid is dried in place under an air stream for 10 min to obtain the title compound (1.16 g, 91.7% yield) as an off white crystalline solid. ES/MS (m/z): 367.0 (M+H).

X-Ray Powder Diffraction (XRPD)

The XRPD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2θ.

A sample of Example 1A is characterized by an XRD pattern using CuKa radiation as having diffraction peaks (2θ values) as described in Table 1 below, and in particular having peaks at 20.7° in combination with one or more of the peaks selected from the group consisting of 16.0°, 15.6°, and 17.3°; with a tolerance for the diffraction angles of 0.2 degrees.

TABLE 1

X-ray powder diffraction peaks of the crystalline compound of Example 1A; (3S)-3-[(1R)-1-[4-[2-[(2,6-dimethyl-4-pyridyl)oxy]ethyl]phenyl]ethyl]-3-methyl-pyrrolidine-2,5-dione mesylate

| Peak | Angle (° θ) +/− 0.2° | Relative Intensity (% of most intense peak) |
|---|---|---|
| 1 | 11.5 | 11.8% |
| 2 | 13.7 | 13.9% |
| 3 | 14.2 | 8.9% |
| 4 | 15.6 | 72.7% |
| 5 | 16.0 | 79.3% |
| 6 | 17.3 | 52.6% |
| 7 | 19.2 | 45.6% |
| 8 | 20.7 | 100.0% |
| 9 | 23.5 | 51.9% |
| 10 | 24.0 | 37.1% |

Inhibition of cAMP Production by CGRP Receptor Antagonists

The hCGRP (human calcitonin gene-related peptide) receptor is functionally coupled to the Gαs proteins. Stimulation of hCGRP results in an increased synthesis of intracellular cAMP and can be blocked by the addition of receptor antagonists. Receptor activity is thus a reflection of the amount of cAMP present within cells which can be detected using standard in vitro technology.

Cell Culture: Cultured SK-N-MC neuroblastoma cells that endogenously express the hCGRP receptor (ATCC) are grown in Eagle's Minimum essential medium (HYCLONE™) supplemented with 10% heat-inactivated Fetal bovine serum (FBS;) GIBCO®), Non-Essential Amino Acids (GIBCO®), 1 mM sodium pyruvate, 2 mM L-glutamine, 100 U/mL of penicillin, and 10 μg/mL of streptomycin to about 70% confluency. After providing fresh medium, the cells are incubated at 37° C. overnight. On the day of the assay, cells are detached using ACCUTASE® (MP Biomedicals), resuspended in assay buffer [Hank's Balanced Salt Solution/Dulbecco's phosphate-buffered saline with 100 mg/mL each of $CaCl_2$ and $MgCl_2$ mixed 1:2, 3.3 mM 4-(2-hydroxyethyl)-1-piperazineethanesulfonic acid, 0.03% bovine serum albumin, and 0.5 mM 1-methyl-3-isobutylxanthine (as inhibitor of cAMP)], and seeded 3-5K/well into 384-well, poly-D-lysine coated white plates (BD Biosciences).

Inhibition of cAMP Production: For dose-response studies, compounds are serially diluted 1:3 in dimethyl sulfoxide and then 1:10 into assay buffer. Human CGRP (0.8 nM; Bachem) as a receptor-specific agonist for the hCGRP receptor is mixed with diluted compound and added to the cells as the challenge stimulant at their $EC_{80}$ concentrations.

Data Analysis: The amount of intracellular cAMP is quantitated using HTRF technology (Cisbio) as per vendor instructions. Briefly, cAMP-d2 conjugate and anti-cAMP-cryptate conjugate in lysis buffer are incubated with the treated cells at RT for 90 min. The HTRF signal is immediately detected using an ENVISION® plate reader (PerkinElmer) to calculate the ratio of fluorescence at 665 to 620 nM. The raw data are converted to cAMP amount (pmole/well) using a cAMP standard curve generated for each experiment. Relative $EC_{50}$ values are calculated from the top-bottom range of the concentration response curve using a four-parameter logistic curve fitting program (ACTIVITYBASE® v5.3.1.22 or GENEDATA SCREENER® v12.0.4), and $K_b$ values are estimated as agonist-corrected $IC_{50}$ values using the equation:

$$K_b = (IC_{50})[1+([Agonist]/EC_{50})].$$

Estimated $K_b$ values are reported as mean values ±SEM, averaged from the number of runs (n).

Following the procedure essentially as described above, the compound of Example 1 has a $K_b$ measured at human CGRP as 0.31±0.210 nM (n=16). This demonstrates that the compound of Example 1 is an antagonist of the human CGRP receptor in vitro.

In Vitro Determination of Efflux by ABCB1, Human P-Glycoprotein (Pgp)

Cell Culture: MDCKII cells stably expressing human wild-type ABCB1 (Pgp) are obtained from the Netherlands Cancer Institute (Amsterdam, The Netherlands). MDCK cells are maintained as described previously (Desai et al., Mol Pharm 10:1249-1261, 2013).

Bi-directional transport across MDCK cells: The assay is essentially conducted as described previously (Desai et al., Mol Pharm 10:1249-1261, 2013). Transport is measured in both directions across uninhibited and inhibited cell monolayers using a substrate concentration of 5 μM diluted from a 10 mM DMSO stock solution (final DMSO concentration of 0.05%) and a single 60-min time interval. 2.5 μM of the compound of Example 1 is used to selectively inhibit Pgp.

The apparent permeability coefficients (Papp) are estimated as the slope of the mass transported per 60 min relative to the total recovered mass. The basal-to-apical (B-A)/apical-to-basal (A-B) Papp ratios are calculated in the absence or presence of inhibitor in each cell line for net efflux ratio (NER).

Result: The NER of the compound of Example 1 for efflux by Pgp is determined to be 4.1.

In Vivo Determination of Unbound Brain-to-Plasma Partition Coefficient ($K_{p,uu,brain}$) in Rats Unbound brain-to-plasma partition coefficient ($K_{p,uu,brain}$) is one of the key pharmacokinetic parameter for evaluating a compound's ability to cross the blood-brain barrier (BBB) (Hammarlund-Udenaes, M.; Friden, M.; Syvanen, S.; Gupta, A. On the Rate and Extent of Drug Delivery to the Brain. Pharm. Res. 2008, 25 (8), 1737-1750). $K_{p,uu,brain}$ is typically measured in pre-clinical species using the following methodology, and $K_{p,uu,brain}$ values exceeding 0.3 suggest that more than 30% of the unbound compound in plasma crosses the BBB.

Study populations: Animal studies are performed under protocols approved by the Covance Institutional Animal Care and Use Committee. Male Sprague-Dawley rats weighing 250-350 g are obtained from Harlan Sprague Dawley Inc. (Indianapolis, Ind.). Animals have access to food and water ad libitum before and during the study.

Dose administration: Animals each receive 10 mg/kg of the CGRP receptor antagonist compound of Example 1, administered orally in 10 ml/kg of hydroxyethylcellulose 1% w/v/polysorbate 80 0.25% v/v/Antifoam 1510-US 0.05% v/v/in purified water (probe sonicated).

Pharmacokinetic sampling: Three animals per time point are used. The blood (by cardiac puncture) and brain samples are collected at 0.5 and 2 h post dose. The blood samples are treated with $K_3$-EDTA anticoagulant, and plasma is obtained by centrifugation at 1600 g for 10 minutes. The brain samples are weighed and homogenized, without perfusion. All samples are stored at −70° C. until analysis by LC-MS/MS to determine the concentration of the compound of Example 1 in plasma and brain at each time point.

Determination of plasma and brain protein binding: Rat plasma and brain homogenate protein in vitro binding is determined using equilibrium dialysis, as described elsewhere [Zamek-Gliszczynski et al., J Pharm Sci, 101:1932-1940, 2012]. The results are reported as fraction unbound in plasma ($f_{u,plasma}$) and brain ($f_{u,brain}$), which are then utilized to calculate $K_{p,uu,brain}$, as described in Table 2. Rat $f_{u,plasma}$ and $f_{u,brain}$ of the compound of Example 1 are determined to be 0.277 and 0.126, respectively.

Analysis and Results:

$K_{p,uu,brain}$ is calculated for each time point from the expression below where individual components are derived from a combination of in vitro and in vivo measurements carried out as described above:

$$K_{p,uu,brain} = \frac{C_{u,brain}}{C_{u,plasma}} = \frac{C_{total,brain}}{C_{total,plasma}} \cdot \frac{f_{u,brain}}{f_{u,plasma}}$$

where $C_{total,brain}$, $C_{u,brain}$, $C_{total,plasma}$ and $C_{u,plasma}$ are total and unbound brain and plasma concentrations, and $f_{u,brain}$ and $f_{u,plasma}$ are fractions unbound in brain and plasma, respectively.

The plasma and brain concentrations for the compound of Example 1 are provided in Table 2. The results are expressed as mean±standard deviation.

TABLE 2

Plasma and brain concentrations of the compound of Example 1 post 10 mg/kg oral dose in male Sprague-Dawley rats. The results are expressed as mean +/− standard deviation.

| Time point (hr) | Total brain conc. ($C_{total,brain}$) (nM) | Total plasma conc. ($C_{total,plasma}$) (nM) | Unbound brain conc. ($C_{u,brain}$) (nM)* | Unbound plasma conc. ($C_{u,plasma}$) (nM)^ | $K_{p,uu,brain}$ |
|---|---|---|---|---|---|
| 0.5 | 365 ± 67 | 497 ± 69 | 46 ± 9 | 138 ± 19 | 0.34 ± 0.05 |
| 2.0 | 405 ± 83 | 531 ± 129 | 51 ± 10 | 147 ± 36 | 0.35 ± 0.01 |

*Using rat $f_{u,brain}$ value of 0.126 and ^rat $f_{u,plasma}$ value of 0.277, as described above.

The unbound brain concentrations of the compound of Example 1 at 0.5 and 2 hours post oral dose of 10 mpk in male Sprague-Dawley rats are determined to be 46 ±9 nM and 51±10 nM, respectively. Kp,uu,brain of the compound of Example 1 at 0.5 and 2 hours post oral dose of 10 mpk in male Sprague-Dawley rats is determined to be 0.34±0.05 and 0.35±0.01, respectively.

We claim:

1. A compound of the formula:

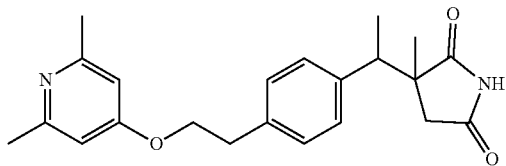 [SMILES: Cc1cc(OCCc2ccc(C(C)C3(C)CC(=O)NC3=O)cc2)cc(C)n1]

or a pharmaceutically acceptable salt thereof.

2. The compound or salt according to claim 1 of the formula:

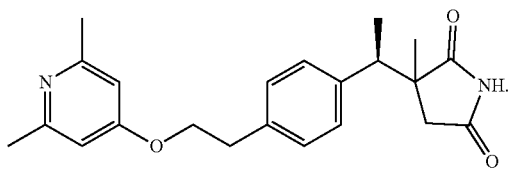 [SMILES: Cc1cc(OCCc2ccc([C@@H](C)C3(C)CC(=O)NC3=O)cc2)cc(C)n1]

3. The compound or salt according to claim 1 of the formula:

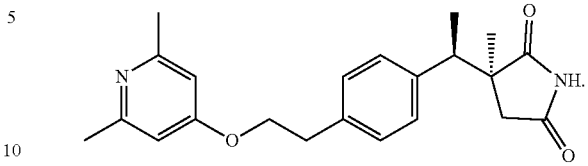

4. The compound according to claim 3 which is:

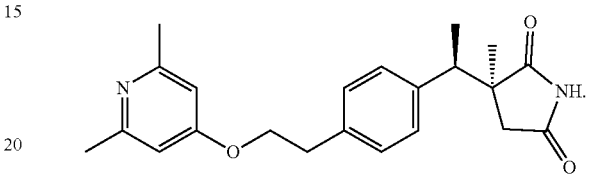

5. The compound according to claim 3 which is (3S)-3-[(1R)-1-[4-[2-[(2,6-dimethyl-4-pyridyl)oxy]ethyl]phenyl]ethyl]-3-methyl-pyrrolidine-2,5-dione mesylate.

6. The compound according to claim 5 which is crystalline.

7. The crystalline compound according to claim 6 which is characterized by a peak in the X-ray powder diffraction spectrum at diffraction angle 2-theta of 20.7° in combination with one or more peaks selected from the group consisting of 16.0°, 15.6°, and 17.3°, with a tolerance for the diffraction angles of 0.2 degrees.

8. A method of treating migraine in a patient, comprising administering to a patient in need thereof an effective amount of a compound or salt of claim 1.

9. A pharmaceutical composition, comprising a compound or salt according to claim 1 with one or more pharmaceutically acceptable carriers, diluents, or excipients.

10. A process for preparing a pharmaceutical composition, comprising admixing a compound or salt according to claim 1 with one or more pharmaceutically acceptable carriers, diluents, or excipients.

11. A pharmaceutical composition, comprising a compound or salt according to claim 3 with one or more pharmaceutically acceptable carriers, diluents, or excipients.

* * * * *